United States Patent
Daniel et al.

(10) Patent No.: US 10,930,174 B2
(45) Date of Patent: Feb. 23, 2021

(54) SYSTEMS AND METHODS PROVIDING A COMPUTERIZED EYEWEAR DEVICE TO AID IN WELDING

(71) Applicant: Lincoln Global, Inc., Santa Fe Springs, CA (US)

(72) Inventors: Joseph Allen Daniel, Sagamore Hills, OH (US); William Thomas Matthews, Chesterland, OH (US)

(73) Assignee: LINCOLN GLOBAL, INC., Santa Fe Springs, CA (US)

( * ) Notice: Subject to any disclaimer, the term of this patent is extended or adjusted under 35 U.S.C. 154(b) by 612 days.

(21) Appl. No.: 15/660,525

(22) Filed: Jul. 26, 2017

(65) Prior Publication Data

US 2017/0323584 A1 Nov. 9, 2017

Related U.S. Application Data

(63) Continuation-in-part of application No. 15/245,535, filed on Aug. 24, 2016, now Pat. No. 10,373,524.
(Continued)

(51) Int. Cl.
*B23K 9/09* (2006.01)
*G02B 27/01* (2006.01)
(Continued)

(52) U.S. Cl.
CPC .............. *G09B 19/24* (2013.01); *A61F 9/06* (2013.01); *B23K 9/0953* (2013.01);
(Continued)

(58) Field of Classification Search
CPC ...... B23K 9/0953; B23K 9/0956; B23K 9/10; B23K 9/1006; B23K 9/32; B23K 9/321;
(Continued)

(56) References Cited

U.S. PATENT DOCUMENTS

| 317,063 A | 5/1885 | Wittenstrom |
| 428,459 A | 5/1890 | Coffin |

(Continued)

FOREIGN PATENT DOCUMENTS

| CA | 2698078 A1 | 9/2011 |
| CN | 101209512 A | 7/2008 |

(Continued)

OTHER PUBLICATIONS

"High Performance Computer Architectures_ A Historical Perspective," downloaded May 5, 2016.
(Continued)

*Primary Examiner* — Brian W Jennison
(74) *Attorney, Agent, or Firm* — David J. Muzilla

(57) ABSTRACT

A system to support communication and control in a welding environment is disclosed. In one embodiment the system includes an internet-of-things (IoT) technology platform configured to provide scalable, interoperable, and secure communication connections between a plurality of disparate devices within a welding environment. The system also includes a welding power source configured to communicate with the IoT technology platform. The system further includes a computerized eyewear device. The computerized eyewear device includes a control and communication circuitry configured to communicate with the welding power source via the IoT technology platform. The computerized eyewear device also includes a transparent display configured to display information received from the welding power source via the IoT technology platform while allowing a user to view a surrounding portion of the welding environment through the transparent display.

19 Claims, 7 Drawing Sheets

Related U.S. Application Data which is a continuation of application No. 14/105,758, filed on Dec. 13, 2013, now Pat. No. 10,748,447.

(60) Provisional application No. 61/827,248, filed on May 24, 2013.

(51) Int. Cl.

| | | |
|---|---|---|
| *G09B 19/24* | (2006.01) | |
| *G09B 19/00* | (2006.01) | |
| *B23K 9/095* | (2006.01) | |
| *G06K 9/00* | (2006.01) | |
| *B23K 9/32* | (2006.01) | |
| *G09B 9/00* | (2006.01) | |
| *B23K 37/00* | (2006.01) | |
| *B23K 9/10* | (2006.01) | |
| *G09B 5/02* | (2006.01) | |
| *A61F 9/06* | (2006.01) | |
| *G06F 3/16* | (2006.01) | |
| *G06F 3/0488* | (2013.01) | |

(52) U.S. Cl.
CPC .......... *B23K 9/0956* (2013.01); *B23K 9/10* (2013.01); *B23K 9/1006* (2013.01); *B23K 9/32* (2013.01); *B23K 9/321* (2013.01); *B23K 9/322* (2013.01); *B23K 37/00* (2013.01); *G02B 27/0172* (2013.01); *G02B 27/0176* (2013.01); *G06K 9/00* (2013.01); *G06K 9/00671* (2013.01); *G09B 5/02* (2013.01); *G09B 9/00* (2013.01); *G09B 19/003* (2013.01); *G02B 27/017* (2013.01); *G02B 2027/014* (2013.01); *G02B 2027/0138* (2013.01); *G02B 2027/0158* (2013.01); *G02B 2027/0178* (2013.01); *G02B 2027/0187* (2013.01); *G06F 3/04883* (2013.01); *G06F 3/167* (2013.01)

(58) Field of Classification Search
CPC ........ B23K 9/322; B23K 37/00; G09B 19/24; G09B 5/02; G09B 9/00; G09B 19/003; G02B 27/0172; G02B 27/0176; G02B 27/017; G02B 2027/0138; G02B 2027/0178

See application file for complete search history.

(56) References Cited

U.S. PATENT DOCUMENTS

| | | |
|---|---|---|
| 483,428 A | 9/1892 | Coffin |
| 1,159,119 A | 11/1915 | Springer |
| D140,630 S | 3/1945 | Garibay |
| D142,377 S | 9/1945 | Dunn |
| D152,049 S | 12/1948 | Welch, Jr. |
| 2,681,969 A | 6/1954 | Burke |
| D174,208 S | 3/1955 | Abildgaard |
| 2,728,838 A | 12/1955 | Barnes |
| D176,942 S | 2/1956 | Cross |
| 2,894,086 A | 7/1959 | Rizer |
| 3,035,155 A | 5/1962 | Hawk |
| 3,059,519 A | 10/1962 | Stanton |
| 3,356,823 A | 12/1967 | Waters et al. |
| 3,555,239 A | 1/1971 | Kerth |
| 3,621,177 A | 11/1971 | McPherson et al. |
| 3,654,421 A | 4/1972 | Streetman et al. |
| 3,739,140 A | 6/1973 | Rotilio |
| 3,866,011 A | 2/1975 | Cole |
| 3,867,769 A | 2/1975 | Schow et al. |
| 3,904,845 A | 9/1975 | Minkiewicz |
| 3,988,913 A | 11/1976 | Metcalfe et al. |
| D243,459 S | 2/1977 | Bliss |
| 4,024,371 A | 5/1977 | Drake |
| 4,041,615 A | 8/1977 | Whitehill |
| D247,421 S | 3/1978 | Driscoll |
| 4,124,944 A | 11/1978 | Blair |
| 4,132,014 A | 1/1979 | Schow |
| 4,237,365 A | 12/1980 | Lambros et al. |
| 4,280,041 A | 7/1981 | Kiessling et al. |
| 4,280,042 A | 7/1981 | Berger et al. |
| 4,280,137 A | 7/1981 | Ashida et al. |
| 4,314,125 A | 2/1982 | Nakamura |
| 4,354,087 A | 10/1982 | Osterlitz |
| 4,359,622 A | 11/1982 | Dostoomian et al. |
| 4,375,026 A | 2/1983 | Kearney |
| 4,410,787 A | 10/1983 | Kremers et al. |
| 4,429,266 A | 1/1984 | Tradt |
| 4,452,589 A | 6/1984 | Denison |
| D275,292 S | 8/1984 | Bouman |
| D277,761 S | 2/1985 | Korovin et al. |
| 4,525,619 A | 6/1985 | Ide et al. |
| D280,329 S | 8/1985 | Bouman |
| 4,611,111 A | 9/1986 | Baheti et al. |
| 4,616,326 A | 10/1986 | Meier et al. |
| 4,629,860 A | 12/1986 | Lindbom |
| 4,677,277 A | 6/1987 | Cook et al. |
| 4,680,014 A | 7/1987 | Paton et al. |
| 4,689,021 A | 8/1987 | Vasiliev et al. |
| 4,707,582 A | 11/1987 | Beyer |
| 4,716,273 A | 12/1987 | Paton et al. |
| D297,704 S | 9/1988 | Bulow |
| 4,867,685 A | 9/1989 | Brush et al. |
| 4,877,940 A | 10/1989 | Bangs et al. |
| 4,897,521 A | 1/1990 | Burr |
| 4,907,973 A | 3/1990 | Hon |
| 4,931,018 A | 6/1990 | Herbst et al. |
| 4,973,814 A | 11/1990 | Kojima et al. |
| 4,998,050 A | 3/1991 | Nishiyama et al. |
| 5,034,593 A | 7/1991 | Rice et al. |
| 5,061,841 A | 10/1991 | Richardson |
| 5,089,914 A | 2/1992 | Prescott |
| 5,192,845 A | 3/1993 | Kirmsse et al. |
| 5,206,472 A | 4/1993 | Myking et al. |
| 5,266,930 A | 11/1993 | Ichikawa et al. |
| 5,285,916 A | 2/1994 | Ross |
| 5,305,183 A | 4/1994 | Teynor |
| 5,320,538 A | 6/1994 | Baum |
| 5,337,611 A | 8/1994 | Fleming et al. |
| 5,360,156 A | 11/1994 | Ishizaka et al. |
| 5,360,960 A | 11/1994 | Shirk |
| 5,370,071 A | 12/1994 | Ackermann |
| D359,296 S | 6/1995 | Witherspoon |
| 5,424,634 A | 6/1995 | Goldfarb et al. |
| 5,436,638 A | 7/1995 | Bolas et al. |
| 5,464,957 A | 11/1995 | Kidwell et al. |
| D365,583 S | 12/1995 | Viken |
| 5,562,843 A | 10/1996 | Yasumoto |
| 5,662,822 A | 9/1997 | Tada |
| 5,670,071 A | 9/1997 | Ueyama et al. |
| 5,676,503 A | 10/1997 | Lang |
| 5,676,867 A | 10/1997 | Van Allen |
| 5,708,253 A | 1/1998 | Bloch et al. |
| 5,710,405 A | 1/1998 | Solomon et al. |
| 5,719,369 A | 2/1998 | White et al. |
| D392,534 S | 3/1998 | Degen et al. |
| 5,728,991 A | 3/1998 | Takada et al. |
| 5,751,258 A | 5/1998 | Fergason et al. |
| D395,296 S | 6/1998 | Kaye et al. |
| D396,238 S | 7/1998 | Schmitt |
| 5,781,258 A | 7/1998 | Dabral et al. |
| 5,823,785 A | 10/1998 | Matherne, Jr. |
| 5,835,077 A | 11/1998 | Dao et al. |
| 5,835,277 A | 11/1998 | Hegg |
| 5,845,053 A | 12/1998 | Watanabe et al. |
| 5,877,777 A | 3/1999 | Colwell |
| 5,916,464 A | 6/1999 | Geiger |
| 5,963,891 A | 10/1999 | Walker et al. |
| 6,008,470 A | 12/1999 | Zhang et al. |
| 6,037,948 A | 3/2000 | Liepa |
| 6,049,059 A | 4/2000 | Kim |
| 6,051,805 A | 4/2000 | Vaidya et al. |
| 6,114,645 A | 9/2000 | Burgess |
| 6,155,475 A | 12/2000 | Ekelof et al. |

(56) References Cited

U.S. PATENT DOCUMENTS

| | | |
|---|---|---|
| 6,155,928 A | 12/2000 | Burdick |
| 6,230,327 B1 | 5/2001 | Briand et al. |
| 6,236,013 B1 | 5/2001 | Delzenne |
| 6,236,017 B1 | 5/2001 | Smartt et al. |
| 6,242,711 B1 | 6/2001 | Cooper |
| 6,271,500 B1 | 8/2001 | Hirayama et al. |
| 6,330,938 B1 | 12/2001 | Herve et al. |
| 6,330,966 B1 | 12/2001 | Eissfeller |
| 6,331,848 B1 | 12/2001 | Stove et al. |
| D456,428 S | 4/2002 | Aronson, II et al. |
| 6,373,465 B2 | 4/2002 | Jolly et al. |
| D456,828 S | 5/2002 | Aronson, II et al. |
| D461,383 S | 8/2002 | Blackburn |
| 6,441,342 B1 | 8/2002 | Hsu |
| 6,445,964 B1 | 9/2002 | White et al. |
| 6,492,618 B1 | 12/2002 | Flood et al. |
| 6,506,997 B2 | 1/2003 | Matsuyama |
| 6,552,303 B1 | 4/2003 | Blankenship et al. |
| 6,560,029 B1 | 5/2003 | Dobbie et al. |
| 6,563,489 B1 | 5/2003 | Latypov et al. |
| 6,568,846 B1 | 5/2003 | Cote et al. |
| D475,726 S | 6/2003 | Suga et al. |
| 6,572,379 B1 | 6/2003 | Sears et al. |
| 6,583,386 B1 | 6/2003 | Ivkovich |
| 6,621,049 B2 | 9/2003 | Suzuki |
| 6,624,388 B1 | 9/2003 | Blankenship et al. |
| D482,171 S | 11/2003 | Vui et al. |
| 6,647,288 B2 | 11/2003 | Madill et al. |
| 6,649,858 B2 | 11/2003 | Wakeman |
| 6,655,645 B1 | 12/2003 | Lu et al. |
| 6,660,965 B2 | 12/2003 | Simpson |
| 6,697,701 B2 | 2/2004 | Hillen et al. |
| 6,697,770 B1 | 2/2004 | Nagetgaal |
| 6,703,585 B2 | 3/2004 | Suzuki |
| 6,708,385 B1 | 3/2004 | Lemelson |
| 6,710,298 B2 | 3/2004 | Eriksson |
| 6,710,299 B2 | 3/2004 | Blankenship et al. |
| 6,715,502 B1 | 4/2004 | Rome et al. |
| D490,347 S | 5/2004 | Meyers |
| 6,730,875 B2 | 5/2004 | Hsu |
| 6,734,393 B1 | 5/2004 | Friedl et al. |
| 6,744,011 B1 | 6/2004 | Hu et al. |
| 6,750,428 B2 | 6/2004 | Okamoto et al. |
| 6,765,584 B1 | 7/2004 | Wloka et al. |
| 6,768,974 B1 | 7/2004 | Nanjundan et al. |
| 6,772,802 B2 | 8/2004 | Few |
| 6,788,442 B1 | 9/2004 | Potin et al. |
| 6,795,778 B2 | 9/2004 | Dodge et al. |
| 6,798,974 B1 | 9/2004 | Nakano et al. |
| 6,857,553 B1 | 2/2005 | Hartman et al. |
| 6,858,817 B2 | 2/2005 | Blankenship et al. |
| 6,865,926 B2 | 3/2005 | O'Brien et al. |
| D504,449 S | 4/2005 | Butchko |
| 6,920,371 B2 | 7/2005 | Hillen et al. |
| 6,940,037 B1 | 9/2005 | Kovacevic et al. |
| 6,940,039 B2 | 9/2005 | Blankenship et al. |
| 7,021,937 B2 | 4/2006 | Simpson et al. |
| 7,024,342 B1 | 4/2006 | Waite et al. |
| 7,126,078 B2 | 10/2006 | Demers et al. |
| 7,132,617 B2 | 11/2006 | Lee et al. |
| 7,170,032 B2 | 1/2007 | Flood |
| 7,194,447 B2 | 3/2007 | Harvey et al. |
| 7,247,814 B2 | 7/2007 | Ott |
| D555,446 S | 11/2007 | Picaza Ibarrondo et al. |
| 7,315,241 B1 | 1/2008 | Daily et al. |
| D561,973 S | 2/2008 | Kinsley et al. |
| 7,353,715 B2 | 4/2008 | Myers |
| 7,363,137 B2 | 4/2008 | Brant et al. |
| 7,375,304 B2 | 5/2008 | Kainec et al. |
| 7,381,923 B2 | 6/2008 | Gordon et al. |
| 7,414,595 B1 | 8/2008 | Muffler |
| 7,465,230 B2 | 12/2008 | LeMay et al. |
| 7,478,108 B2 | 1/2009 | Townsend et al. |
| D587,975 S | 3/2009 | Aronson, II et al. |
| 7,516,022 B2 | 4/2009 | Lee et al. |
| 7,557,327 B2 | 7/2009 | Matthews |
| 7,580,821 B2 | 8/2009 | Schirm et al. |
| D602,057 S | 10/2009 | Osicki |
| 7,621,171 B2 | 11/2009 | O'Brien |
| D606,102 S | 12/2009 | Bender et al. |
| 7,643,890 B1 | 1/2010 | Hillen et al. |
| 7,687,741 B2 | 3/2010 | Kainec et al. |
| D614,217 S | 4/2010 | Peters et al. |
| D615,573 S | 5/2010 | Peters et al. |
| 7,817,162 B2 | 10/2010 | Bolick et al. |
| 7,853,645 B2 | 12/2010 | Brown et al. |
| D631,074 S | 1/2011 | Peters et al. |
| 7,874,921 B2 | 1/2011 | Baszucki et al. |
| 7,970,172 B1 | 6/2011 | Hendrickson |
| 7,972,129 B2 | 7/2011 | O'Donoghue |
| 7,991,587 B2 | 8/2011 | Ihn |
| 8,069,017 B2 | 11/2011 | Hallquist |
| 8,224,881 B1 | 7/2012 | Spear et al. |
| 8,248,324 B2 | 8/2012 | Nangle |
| 8,265,886 B2 | 9/2012 | Bisiaux et al. |
| 8,274,013 B2 | 9/2012 | Wallace |
| 8,287,522 B2 | 10/2012 | Moses et al. |
| 8,316,462 B2 | 11/2012 | Becker et al. |
| 8,363,048 B2 | 1/2013 | Gering |
| 8,365,603 B2 | 2/2013 | Lesage et al. |
| 8,512,043 B2 | 8/2013 | Choquet |
| 8,569,646 B2 | 10/2013 | Daniel et al. |
| 8,680,434 B2 | 3/2014 | Stoger et al. |
| 8,747,116 B2 | 6/2014 | Zboray et al. |
| 8,777,629 B2 | 7/2014 | Kreindl et al. |
| RE45,062 E | 8/2014 | Maguire, Jr. |
| 8,851,896 B2 | 10/2014 | Wallace et al. |
| 8,860,760 B2 | 10/2014 | Chen |
| 8,915,740 B2 | 12/2014 | Zboray |
| RE45,398 E | 3/2015 | Wallace |
| 8,992,226 B1 | 3/2015 | Leach et al. |
| 9,011,154 B2 | 4/2015 | Kindig et al. |
| 9,293,056 B2 | 3/2016 | Zboray et al. |
| 9,293,057 B2 | 3/2016 | Zboray et al. |
| 9,318,026 B2 | 4/2016 | Peters et al. |
| 9,323,056 B2 | 4/2016 | Williams |
| 9,522,437 B2 | 12/2016 | Pfeifer |
| 2001/0045808 A1 | 11/2001 | Hietmann et al. |
| 2001/0052893 A1 | 12/2001 | Jolly et al. |
| 2002/0032553 A1 | 3/2002 | Simpson et al. |
| 2002/0046999 A1 | 4/2002 | Veikkolainen et al. |
| 2002/0050984 A1 | 5/2002 | Roberts |
| 2002/0085843 A1 | 7/2002 | Mann |
| 2002/0175897 A1 | 11/2002 | Pelosi |
| 2003/0000931 A1 | 1/2003 | Ueda et al. |
| 2003/0011673 A1 | 1/2003 | Eriksson |
| 2003/0025884 A1 | 2/2003 | Hamana et al. |
| 2003/0075534 A1 | 4/2003 | Okamoto et al. |
| 2003/0106787 A1 | 6/2003 | Santilli |
| 2003/0111451 A1 | 6/2003 | Blankenship et al. |
| 2003/0172032 A1 | 9/2003 | Choquet |
| 2003/0186199 A1 | 10/2003 | McCool et al. |
| 2003/0223592 A1 | 12/2003 | Deruginsky et al. |
| 2003/0234885 A1 | 12/2003 | Pilu |
| 2004/0020907 A1 | 2/2004 | Zauner et al. |
| 2004/0035990 A1 | 2/2004 | Ackeret |
| 2004/0050824 A1 | 3/2004 | Samler |
| 2004/0088071 A1 | 5/2004 | Kouno et al. |
| 2004/0140301 A1 | 7/2004 | Blankenship et al. |
| 2004/0181382 A1 | 9/2004 | Hu et al. |
| 2004/0217096 A1 | 11/2004 | Lipnevicius |
| 2005/0007504 A1 | 1/2005 | Fergason |
| 2005/0017152 A1 | 1/2005 | Fergason |
| 2005/0029326 A1 | 2/2005 | Henrickson |
| 2005/0046584 A1 | 3/2005 | Breed |
| 2005/0050168 A1 | 3/2005 | Wen et al. |
| 2005/0101767 A1 | 5/2005 | Clapham et al. |
| 2005/0103766 A1 | 5/2005 | Iizuka et al. |
| 2005/0103767 A1 | 5/2005 | Kainec et al. |
| 2005/0109735 A1 | 5/2005 | Flood |
| 2005/0128186 A1 | 6/2005 | Shahoian et al. |
| 2005/0133488 A1 | 6/2005 | Blankenship et al. |
| 2005/0159840 A1 | 7/2005 | Lin et al. |
| 2005/0163364 A1 | 7/2005 | Beck et al. |

(56) References Cited

U.S. PATENT DOCUMENTS

| | | |
|---|---|---|
| 2005/0189336 A1 | 9/2005 | Ku |
| 2005/0199602 A1 | 9/2005 | Kaddani et al. |
| 2005/0230573 A1 | 10/2005 | Ligertwood |
| 2005/0252897 A1 | 11/2005 | Hsu et al. |
| 2005/0275913 A1 | 12/2005 | Vesely et al. |
| 2005/0275914 A1 | 12/2005 | Vesely et al. |
| 2006/0014130 A1 | 1/2006 | Weinstein |
| 2006/0076321 A1 | 4/2006 | Maev et al. |
| 2006/0136183 A1 | 6/2006 | Choquet |
| 2006/0142656 A1 | 6/2006 | Malackowski et al. |
| 2006/0154226 A1 | 7/2006 | Maxfield |
| 2006/0163227 A1 | 7/2006 | Hillen et al. |
| 2006/0166174 A1 | 7/2006 | Rowe et al. |
| 2006/0169682 A1 | 8/2006 | Kainec et al. |
| 2006/0173619 A1 | 8/2006 | Brant et al. |
| 2006/0189260 A1 | 8/2006 | Sung |
| 2006/0207980 A1 | 9/2006 | Jacovetty et al. |
| 2006/0213892 A1 | 9/2006 | Ott |
| 2006/0214924 A1 | 9/2006 | Kawamoto et al. |
| 2006/0226137 A1 | 10/2006 | Huismann et al. |
| 2006/0252543 A1 | 11/2006 | Van Noland et al. |
| 2006/0258447 A1 | 11/2006 | Baszucki et al. |
| 2007/0034611 A1 | 2/2007 | Drius et al. |
| 2007/0038400 A1 | 2/2007 | Lee et al. |
| 2007/0045488 A1 | 3/2007 | Shin |
| 2007/0080153 A1* | 4/2007 | Albrecht ............ B23K 9/10 219/130.01 |
| 2007/0088536 A1 | 4/2007 | Ishikawa |
| 2007/0112889 A1 | 5/2007 | Cook et al. |
| 2007/0198117 A1 | 8/2007 | Wajihuddin |
| 2007/0209586 A1 | 9/2007 | Ebensberger et al. |
| 2007/0211026 A1 | 9/2007 | Ohta |
| 2007/0221797 A1 | 9/2007 | Thompson et al. |
| 2007/0256503 A1 | 11/2007 | Wong et al. |
| 2007/0277611 A1 | 12/2007 | Portzgen et al. |
| 2007/0291035 A1 | 12/2007 | Vesely et al. |
| 2008/0021311 A1 | 1/2008 | Goldbach |
| 2008/0031774 A1 | 2/2008 | Magnant et al. |
| 2008/0038702 A1 | 2/2008 | Choquet |
| 2008/0061113 A9 | 3/2008 | Seki et al. |
| 2008/0078811 A1 | 4/2008 | Hillen et al. |
| 2008/0078812 A1 | 4/2008 | Peters et al. |
| 2008/0117203 A1 | 5/2008 | Gering |
| 2008/0120075 A1 | 5/2008 | Wloka |
| 2008/0128398 A1 | 6/2008 | Schneider |
| 2008/0135533 A1 | 6/2008 | Ertmer et al. |
| 2008/0140815 A1 | 6/2008 | Brant et al. |
| 2008/0149686 A1 | 6/2008 | Daniel et al. |
| 2008/0203075 A1 | 8/2008 | Feldhausen et al. |
| 2008/0233550 A1 | 9/2008 | Solomon |
| 2008/0303197 A1 | 12/2008 | Paquette et al. |
| 2008/0314887 A1 | 12/2008 | Stoger et al. |
| 2009/0015585 A1 | 1/2009 | Klusza |
| 2009/0021514 A1 | 1/2009 | Klusza |
| 2009/0045183 A1 | 2/2009 | Artelsmair et al. |
| 2009/0050612 A1 | 2/2009 | Serruys |
| 2009/0057286 A1 | 3/2009 | Ihara et al. |
| 2009/0152251 A1 | 6/2009 | Dantinne et al. |
| 2009/0173726 A1 | 7/2009 | Davidson et al. |
| 2009/0184098 A1 | 7/2009 | Daniel et al. |
| 2009/0200281 A1 | 8/2009 | Hampton |
| 2009/0200282 A1 | 8/2009 | Hampton |
| 2009/0231423 A1* | 9/2009 | Becker ............ A61F 9/06 348/82 |
| 2009/0259444 A1 | 10/2009 | Dolansky et al. |
| 2009/0298024 A1 | 12/2009 | Batzler et al. |
| 2009/0325699 A1 | 12/2009 | Delgiannidis |
| 2010/0012017 A1 | 1/2010 | Miller |
| 2010/0012637 A1 | 1/2010 | Jaeger |
| 2010/0048273 A1 | 2/2010 | Wallace et al. |
| 2010/0062405 A1 | 3/2010 | Zboray et al. |
| 2010/0062406 A1 | 3/2010 | Zboray et al. |
| 2010/0096373 A1 | 4/2010 | Hillen et al. |
| 2010/0121472 A1 | 5/2010 | Babu et al. |
| 2010/0133247 A1 | 6/2010 | Mazumder et al. |
| 2010/0133250 A1 | 6/2010 | Sardy et al. |
| 2010/0176107 A1 | 7/2010 | Bong |
| 2010/0201803 A1 | 8/2010 | Melikian |
| 2010/0224610 A1* | 9/2010 | Wallace ............ B23K 9/0953 219/137 R |
| 2010/0276396 A1 | 11/2010 | Cooper et al. |
| 2010/0299101 A1 | 11/2010 | Shimada et al. |
| 2010/0307249 A1 | 12/2010 | Lesage et al. |
| 2011/0006047 A1 | 1/2011 | Penrod et al. |
| 2011/0060568 A1 | 3/2011 | Goldfine et al. |
| 2011/0091846 A1 | 4/2011 | Kreindl et al. |
| 2011/0114615 A1 | 5/2011 | Daniel et al. |
| 2011/0116076 A1 | 5/2011 | Chantry et al. |
| 2011/0117527 A1 | 5/2011 | Conrardy et al. |
| 2011/0122495 A1 | 5/2011 | Togashi |
| 2011/0183304 A1 | 7/2011 | Wallace et al. |
| 2011/0187746 A1 | 8/2011 | Suto et al. |
| 2011/0220616 A1* | 9/2011 | Mehn ............ B23K 9/291 219/74 |
| 2011/0248864 A1 | 10/2011 | Becker et al. |
| 2011/0284500 A1* | 11/2011 | Rappl ............ B23K 9/1006 219/74 |
| 2011/0290765 A1 | 12/2011 | Albrecht et al. |
| 2011/0316516 A1 | 12/2011 | Schiefermuller et al. |
| 2012/0122062 A1 | 5/2012 | Yang et al. |
| 2012/0180180 A1* | 7/2012 | Steve ............ A61F 9/067 2/12 |
| 2012/0189993 A1 | 7/2012 | Kindig et al. |
| 2012/0291172 A1 | 11/2012 | Wills et al. |
| 2012/0298640 A1 | 11/2012 | Conrardy et al. |
| 2013/0026150 A1 | 1/2013 | Chantry et al. |
| 2013/0040270 A1 | 2/2013 | Albrecht |
| 2013/0044042 A1 | 2/2013 | Olsson et al. |
| 2013/0049976 A1 | 2/2013 | Maggiore |
| 2013/0075380 A1* | 3/2013 | Albrech ............ B23K 9/1006 219/137 R |
| 2013/0182070 A1 | 7/2013 | Peters et al. |
| 2013/0183645 A1 | 7/2013 | Wallace et al. |
| 2013/0189657 A1 | 7/2013 | Wallace et al. |
| 2013/0189658 A1 | 7/2013 | Peters et al. |
| 2013/0206741 A1* | 8/2013 | Pfeifer ............ B23K 9/095 219/130.01 |
| 2013/0209976 A1 | 8/2013 | Postlethwaite et al. |
| 2013/0215281 A1* | 8/2013 | Hobby ............ H04N 7/185 348/207.1 |
| 2013/0230832 A1 | 9/2013 | Peters et al. |
| 2013/0231980 A1 | 9/2013 | Elgart et al. |
| 2013/0291271 A1* | 11/2013 | Becker ............ G06F 3/005 2/8.2 |
| 2013/0327747 A1 | 12/2013 | Dantinne et al. |
| 2014/0017642 A1 | 1/2014 | Postlethwaite et al. |
| 2014/0038143 A1 | 2/2014 | Daniel et al. |
| 2014/0051358 A1 | 2/2014 | Dina et al. |
| 2014/0065584 A1 | 3/2014 | Wallace et al. |
| 2014/0134579 A1 | 5/2014 | Becker |
| 2014/0134580 A1 | 5/2014 | Becker |
| 2014/0205976 A1* | 7/2014 | Peters ............ G09B 5/02 434/234 |
| 2014/0263224 A1 | 9/2014 | Becker |
| 2014/0272835 A1 | 9/2014 | Becker |
| 2014/0272836 A1 | 9/2014 | Becker |
| 2014/0272837 A1 | 9/2014 | Becker |
| 2014/0272838 A1 | 9/2014 | Becker |
| 2014/0312020 A1 | 10/2014 | Daniel |
| 2014/0315167 A1 | 10/2014 | Kreindl et al. |
| 2014/0322684 A1 | 10/2014 | Wallace et al. |
| 2014/0346158 A1* | 11/2014 | Matthews ............ G09B 19/003 219/130.01 |
| 2015/0056584 A1 | 2/2015 | Boulware et al. |
| 2015/0056585 A1 | 2/2015 | Boulware et al. |
| 2015/0056586 A1 | 2/2015 | Penrod et al. |
| 2015/0154884 A1 | 6/2015 | Salsich et al. |
| 2015/0209887 A1 | 7/2015 | DeLisio |
| 2015/0228203 A1 | 8/2015 | Kindig |
| 2015/0261015 A1 | 9/2015 | Han et al. |
| 2015/0375323 A1 | 12/2015 | Becker |
| 2016/0045971 A1 | 2/2016 | Holverson |
| 2016/0148098 A1 | 5/2016 | Barhorst et al. |

(56) References Cited

U.S. PATENT DOCUMENTS

| | | | |
|---|---|---|---|
| 2016/0163221 A1 | 6/2016 | Sommers et al. | |
| 2016/0236303 A1* | 8/2016 | Matthews | G09B 5/02 |
| 2016/0250706 A1 | 9/2016 | Beeson et al. | |
| 2016/0267806 A1 | 9/2016 | Hsu et al. | |
| 2016/0365004 A1 | 12/2016 | Matthews et al. | |
| 2017/0046974 A1 | 2/2017 | Becker | |
| 2017/0053557 A1 | 2/2017 | Daniel | |

FOREIGN PATENT DOCUMENTS

| | | |
|---|---|---|
| CN | 101214178 A | 7/2008 |
| CN | 201083660 Y | 7/2008 |
| CN | 101419755 A | 4/2009 |
| CN | 201229711 Y | 4/2009 |
| CN | 101571887 A | 11/2009 |
| CN | 101587659 A | 11/2009 |
| CN | 102014819 A | 4/2011 |
| CN | 102165504 A | 8/2011 |
| CN | 102298858 A | 12/2011 |
| CN | 202684308 U | 1/2013 |
| CN | 103871279 A | 6/2014 |
| CN | 105057869 A | 11/2015 |
| DE | 2833638 A1 | 2/1980 |
| DE | 3046634 A1 | 7/1982 |
| DE | 3244307 A1 | 5/1984 |
| DE | 3522581 A1 | 1/1987 |
| DE | 4037879 A1 | 6/1991 |
| DE | 19615069 A1 | 10/1997 |
| DE | 19739720 C1 | 10/1998 |
| DE | 19834205 A1 | 2/2000 |
| DE | 20009543 U1 | 8/2001 |
| DE | 102005047204 A1 | 4/2007 |
| DE | 102010038902 A1 | 2/2012 |
| DE | 202012013151 U1 | 2/2015 |
| EP | 0108599 A1 | 5/1984 |
| EP | 0127299 A1 | 12/1984 |
| EP | 0145891 A1 | 6/1985 |
| EP | 0319623 A1 | 6/1989 |
| EP | 0852986 A1 | 7/1998 |
| EP | 1 010 490 A1 | 6/2000 |
| EP | 1527852 A1 | 5/2005 |
| EP | 1905533 A2 | 4/2008 |
| ES | 2274736 A1 | 5/2007 |
| FR | 1456780 A | 7/1966 |
| FR | 2827066 A1 | 1/2003 |
| FR | 2926660 A1 | 7/2009 |
| GB | 1455972 A | 11/1976 |
| GB | 1511608 A | 5/1978 |
| GB | 2254172 A | 9/1992 |
| GB | 2435838 A | 9/2007 |
| GB | 2454232 A | 5/2009 |
| JP | 2224877 | 9/1990 |
| JP | 5329645 | 12/1993 |
| JP | 07047471 | 2/1995 |
| JP | 07232270 | 9/1995 |
| JP | 8132274 A | 5/1996 |
| JP | 8150476 | 6/1996 |
| JP | H08505091 A | 6/1996 |
| JP | 11104833 | 4/1999 |
| JP | 2000167666 A | 6/2000 |
| JP | 2000-237872 A | 9/2000 |
| JP | 2001071140 A | 3/2001 |
| JP | 2002278670 A | 9/2002 |
| JP | 2003200372 A | 7/2003 |
| JP | 2003-240562 A | 8/2003 |
| JP | 2003326362 A | 11/2003 |
| JP | 2006006604 A | 1/2006 |
| JP | 2006281270 A | 10/2006 |
| JP | 2007290025 A | 11/2007 |
| JP | 2009500178 A | 1/2009 |
| JP | 2009160636 A | 7/2009 |
| JP | 2010-019646 A | 1/2010 |
| JP | 2012024867 A | 2/2012 |
| KR | 20090010693 A | 1/2009 |
| KR | 20140030644 A | 3/2014 |
| RU | 2008108601 A | 9/2009 |
| SU | 1038963 A1 | 8/1983 |
| SU | 1651309 A1 | 5/1991 |
| WO | WO-9845078 A1 | 10/1998 |
| WO | WO-0112376 A1 | 2/2001 |
| WO | WO-0143910 A1 | 6/2001 |
| WO | WO-0158400 A1 | 8/2001 |
| WO | WO-2005102230 A1 | 11/2005 |
| WO | WO-2006034571 A1 | 4/2006 |
| WO | WO-2007009131 A1 | 1/2007 |
| WO | WO-2007039278 A1 | 4/2007 |
| WO | WO-2009060231 A1 | 5/2009 |
| WO | WO-2009120921 A1 | 10/2009 |
| WO | 2009/137379 A1 | 11/2009 |
| WO | WO-2009149740 A1 | 12/2009 |
| WO | WO-2010000003 A2 | 1/2010 |
| WO | WO-2010020867 A2 | 2/2010 |
| WO | WO-2010020870 A2 | 2/2010 |
| WO | WO-2010044982 A1 | 4/2010 |
| WO | WO-2010091493 A1 | 8/2010 |
| WO | WO-2011045654 A1 | 4/2011 |
| WO | WO-2011058433 A1 | 5/2011 |
| WO | WO-2011067447 A1 | 6/2011 |
| WO | WO-2011097035 A2 | 8/2011 |
| WO | WO-2012082105 A1 | 6/2012 |
| WO | WO-2012143327 A1 | 10/2012 |
| WO | WO-2013014202 A1 | 1/2013 |
| WO | 2013/025672 A2 | 2/2013 |
| WO | WO-2013061518 A1 | 5/2013 |
| WO | WO-2013114189 A1 | 8/2013 |
| WO | WO-2013175079 A1 | 11/2013 |
| WO | WO-2014007830 A1 | 1/2014 |
| WO | WO-2014019045 A1 | 2/2014 |
| WO | WO-2014020386 A1 | 2/2014 |
| WO | 2016/137578 A1 | 9/2016 |
| WO | 2016/144741 A1 | 9/2016 |
| WO | 2012/1327060 A1 | 10/2020 |

OTHER PUBLICATIONS http://homepages.inf.ed.ac.uk/cgi/rni/comparch.pl?Paru/perf.html,Paru/perf-f.html,Paru/menu-76.html.

Abbas, et al., Code Aster (Software) EDR (France) 14 pages, Oct. 2001.

Abbas, et al., Code_Aster; Introduction to Code_Aster; User Manual; Booket U1.0-: Introduction to Code_Aster; Document: U1.02.00; Version 7.4; Jul. 22, 2005.

Abida et al., "Numerical simulation to study the effect of tack welds and root gap on welding deformations and residual stresses of a pipe-flange joint", Faculty of Mechanical Engineering, GIK Institute of Engineering Sciences and Technology, Topi, NWFP, Pakistan. Available on-line Aug. 25, 2005.

Adams, et al., "Adaptively sampled particle fluids," ACM SIGGRAPH 2007 papers, Aug. 5-9, 2007, San Diego, California.

Agren, "Sensor Integration for Robotic Arc Welding;" 1995; vol. 5604C of Dissertations Abstracts International p. 1123; Dissertation Abs Online (Dialog® File 35): © 2012 ProQuest Info& Learning: http://dialogweb.com/cgi/dwclient?req=1331233317524; one (1) page; printed Mar. 8, 2012.

Aidun et al., Penetration in Spot GTA Welds during Centrifugation, Journal of Materials Engineering and Performance vol. 7(5) Oct. 1998—597.

Aidun, D., "Influence of Simulated High-g on the Weld Size of Al—Li Alloy" Elevator Science Ltd.; 2001; 4 pages.

Aiteanu et al., "Generation and Rendering of a Virtual Welding Seam in an Augmented Reality Training Environment" Proceedings of the Sixth IASTED International Conference, Aug. 2006, 8 pages.

Aiteanu, "Virtual and Augmented Reality Supervisor for a New Welding Helmet" Dissertation Nov. 15, 2005.

Aiteanu, et al., "A Step Forward in Manual Welding:; Demonstration of Augmented Reality Helmet" Institute of Automation, University of Bremen,; Germany, Proceedings ofthe Second IEEE and ACM International Symposium on Mixed and; Augmented Reality; 2003; 2 pages.

(56) References Cited

OTHER PUBLICATIONS

Aiteanu, et al., "Computer-Aided Manual Welding Using an Augmented; Reality Supervisor" Sheet Metal Welding Conference XII, Livonia, MI, May 9-12, 2006, 14 pages.
American Welding Society Advance Program of Programs and Events. Nov. 11-14, 2007. 31 pages. Chicago, IL.
American Welding Society Detroit Section, "Sheet Metal Welding Conference XII", May 2006, 11 pages.
American Welding Society, "Vision for Welding Industry"; 41 pages, Estimated Jan. 1998.
American Welding Society, ANSI/A WS D 10.11 MID 10. 11 :2007 Guide for Root Pass Welding of Pipe without Backing Edition: 3rd American Welding Society / Oct. 13, 2006/36 pages ISBN: 0871716445.
American Welding Society, http://www.nsrp.org/6-presentations/ WDVirtual_Welder. pdf (Virtual Reality Welder Training,; Project No. SI051, Navy ManTech Program, Project Review for Ship Tech 2005); 22 pages.; Biloxi, MS.
American Welding Society, https://app.aws.org/conferences/defense/ live index.html (AWS Welding in the Defense; Industry conference schedule, estimated Jan. 2004); 12 pages.
American Welding Society, https://app.aws.org/w/r/www/wj/2005/ 03/WJ_2005_03.pdf (AWS Welding Journal, Mar. 2005; (see, e.g., p. 54)).; 114 pages.
American Welding Society, https://app.aws.org/wj/2004/04/052/njc (AWS Virtual Reality Program to Train Welders for; Shipbuilding, workshop information, 2004); 7 pages.
American Welding Society, https://app.aws.org/wj/2007 /11/WJ200711. pdf (AWS Welding Journal, Nov. 2007); 240 pages.
American Welding Society, Welding Handbook, Welding Science & Technology, Ninth Ed., Copyright 2001. Appendix A "Terms and Definitions".
Antonelli et al, "A Semi-Automated Welding Station Exploiting Human-Robot Interaction," Advanced Manufacturing Systems and Technology (2011) pp. 249-260.
ARC+—Archived Press Release from WayBack Machine from Jan. 31, 2008-Apr. 22, 2013, Page, https://web.archive.org/web/ 20121006041803/http://www.123certification.com/en/article_press/ index.htm, Jan. 21, 2016, 3 pages.
ARC+ simulator; http://www.123arc.com/en/depliant_ang.pdf; Estimated Jan. 2000.
Kenneth Fast; Virtual Welding—A Low Cost Virtual Reality Welder system training system phase II; NSRP ASE Technology Investment Agreement; Feb. 29, 2012; pp. 1-54.
ArcSentry Weld Quality Monitoring System; Native American Technologies, allegedly 2002, 5; pages.
ARS ELECTRONICA LINZ GMBH, Fronius, 2 pages, May 18, 1997.
Arvika Forum Vorstellung Projekt PAARi. BMW Group Virtual Reality Center. 4 pages.; Nuernberg. 2003.
asciencetutor.com, A division of Advanced Science and Automation Corp., VWL (Virtual Welding Lab), 2 pages, 2007.
ASME Definitions, Consumables, Welding Positions, dated Mar. 19, 2001. See http://www.gowelding.com/wp/asme4.htm.
Balijepalli, et al. "Haptic Interfaces for Virtual Environment and Teleoperator Systems," Haptics 2003, Department of Mechanical & Aerospace Engineering, State University of New York at Buffalo, NY.
Bargteil, et al., "A semi-lagrangian contouring method for fluid simulation," ACM Transactions on Graphics, 25(1), 2006.
Bargteil, et al., "A texture synthesis method for liquid animations," In Proceedings of the ACM SIGGRAPH/Eurographics Symposium on Computer Animation, Sep. 2006.
Bender Shipbuilding and Repair Co. Virtual Welding—A Low Cost Virtual Reality Welding; Training System. Proposal submitted pursuant to MSRP Advanced Shipbuilding Enterprise; Research Announcement, Jan. 23, 2008. 28 pages, See also, http://www.nsrp.org/6-; Presentations/WD/020409 Virtual Welding Wilbur.pdf;.
Borzecki, et al., Specialist Committee V.3 Fabrication Technology Committee Mandate, Aug. 20-25, 2006, 49 pages, vol. 2, 16th International Ship and Offshore Structures Congress, Southampton, UK.
Catalina, et al., "Interaction of Porosity with a Planar Solid/Liquid Interface" ("Catalina"), Metallurgical and Materials Transactions, vol. 35A, May 2004, pp. 1525-1538.
ChemWeb.com—Journal of Materials Engineering (printedSep. 26, 2012) (01928041).
Chen, et al., "Self-Learning Fuzzy Neural Networks and Computer Vision for Control of Pulsed GTAW," dated May 1997.
Chentanez, et al., "Liquid simulation on lattice-based tetrahedral meshes." In ACM SIGGRAPH/Eurographics Symposium on Computer Animation 2007, pp. 219-228, Aug. 2007.
Chentanez, et al., "Simultaneous coupling of fluids and deformable bodies," In ACM SIGGRAPH/Eurographics Symposium on Computer Animation, pp. 83-89, Aug. 2006.
Choquet, C., "ARC+: Today's Virtual Reality Solution for Welders" Internet Page, Jan. 1, 2008; 6 pages.
Choquet, C., "ARC+®: Today's Virtual Reality Solution for Welders", Published in Proceedings of the IIW International Conference; Jul. 10-11, 2008; 19 pages.
Clausen, et al., "Simulating liquids and solid-liquid interactions with lagrangian meshes," ACM Transactions on Graphics, 32(2):17:1-15, Apr. 2013. Presented at SIGGRAPH 2013.
Cooperative Research Program, Virtual Reality Welder Training, Summary Report SR 0512, 4 pages, Jul. 2005.
CS Wave, The Virtual Welding Trainer, 6 pages, 2 estimated Jan. 2007.
CS Wave—Manual, "Virtual Welding Workbench User Manual 3.0" estimated Jan. 2007.
CUDA Programming Guide Version 1.1, Nov. 29, 2007.
Da Dalto, et al. "CS Wave, A Virtual learning tool for welding motion", 10 pages, Mar. 14, 2008.
Da Dalto, et al. "CS Wave: Learning welding motion in a virtual environment" Published in Proceedings of the IIW International Conference, Jul. 10-11, 2008.
Desroches, X.; Code-Aster, Note of use for aciculations of welding; Instruction manual U2.03 booklet: Thermomechanical; Document: U2.03.05; Oct. 1, 2003.
D'Huart, et al., "Virtual Environment for Training" 6th International Conference, ITS 20002, Jun. 2002; 6 pages.
Dotson, "Augmented Reality Welding Helmet Prototypes How Awesome the Technology Can Get," Sep. 26, 2012, Retrieved from the Internet: URL:http://siliconangle.com/blog/2012/09/26/augmented-reality-welding-helmet-prototypes-how-awesome-the-technology-can-get/,retrieved on Sep. 26, 2014, 1 page.
Echtler et al, "17 The Intelligent Welding Gun: Augmented Reality for Experimental Vehicle Construction," Virtual and Augmented Reality Applications in Manufacturing (2003) pp. 1-27.
Edison Welding Institute, E-Weld Predictor, 3 pages, 2008.
Eduwelding+, Training Activities with arc+ simulator; Weld Into the Future, Online Welding Simulator—A virtual training environment; 123arc.com; 6 pages, May 2008.
Eduwelding+, Weld Into the Future; Online Welding Seminar—A virtual training environment; 123arc.com; 4 pages, 2005.
Energetics, Inc. "Welding Technology Roadmap", Sep. 2000, 38 pages.
Fast, K. et al., "Virtual Training for Welding", Mixed and Augmented Reality, 2004, ISMAR 2004, Third IEEE and CM International Symposium on Arlington, VA, Nov. 2-5, 2004.
Feldman, et al., "Animating Suspended Particle Explosions". In Proceedings of ACM SIGGRAPH 2003, pp. 708-715, Aug. 2003.
Feldman, et al., "Fluids in deforming meshes" In ACM SIGGRAPH/ Eurographics Symposium on Computer Animation 2005, Jul. 2005.
Fite-Georgel, "Is there a Reality in Industrial Augmented Reality?" 10th IEEE International Symposium on Mixed and Augmented Reality (ISMAR). 10 pages, allegedly 2011.
Foster, et al., "Realistic animation of liquids," Graphical Models and Image Processing, v.58 n.5, p. 471-483, Sep. 1996.
Foster, et al., "Practical animation of liquids," Proceedings of the 28th annual conference on Computer graphics and interactive techniques, p. 23-30, Aug. 2001.

(56) References Cited

OTHER PUBLICATIONS

Garcia-Allende, et al., "Defect Detection in Arc-Welding Processes by Means of the Line-to-Continuum Method and Feature Selection" www.mdpi.com/journal/sensors; Sensors 2009, 9, 7753-7770; DOI; 10.3390/s91007753.

Goktekin, et al., "A Method for Animating Viscoelastic Fluids". ACM Transactions on Graphics (Proc. of ACM SIGGRAPH 2004), 23(3):463-468, 2004.

Graham, "Texture Mapping" Carnegie Mellon University Class 15-462 Computer graphics, Lecture 10 dated Feb. 13, 2003; 53 pages.

Grahn, A., "Interactive Simulation of Contrast Fluid using Smoothed Particle Hydrodynamics," Jan. 1, 2008, Master's Thesis in Computing Science, Umeå University, Department of Computing Science, Umeå, Sweden.

Guu et al., "Technique for Simultaneous Real-Time Measurements of Weld Pool Surface Geometry and Arc Force," Dec. 1992.

Heston, Virtually Welding—raining in a virtual environment gives welding students a leg up, retrieved on Apr. 12, 2010 from: http://www.thefabricator.com/article/arcwelding/virtually-welding.

Hillers, et al., "Augmented Reality—Helmet for the Manual; Welding Process" Institute of Automation, University of Bremen, Germany; 21 pages, 2004.

Hillers, et al., "Direct welding arc observation without harsh flicker," 8 pages, allegedly FABTECH International and AWS welding show, 2007.

Hillers, et al., "Real time Arc-Welding Video Observation System." 62nd International Conference of IIW, Jul. 12-17, 2009, 5 pages Singapore 2009.

Hillers, et al., "TEREBES:; Welding Helmet with AR Capabilities", Institute of Automatic University Bremen; Institute of; Industrial Engineering and Ergonomics, 10 pages, alleqedlv 2004.

Hillis, et al., "Data Parallel Algorithms", Communications of the ACM, Dec. 1986, vol. 29, No. 12, p. 1170.

Hirche, et al. "Hardware Accelerated Per-Pixel Displacement Mapping" University of Tubingen, Germany, Alexander Ehlert, Stefan Guthe, WStlGRfS & Michael Doggett, ATI Research; 8 pages.

Holmberg et al, "Efficient modeling and rendering of turbulent water over natural terrain," In Proceedings of the 2nd international conference on Computer graphics and interactive techniques in Australasia and South East Asia (GRAPHITE '04) 2004.

Sun Yaoming; Application of Micro Computer in Robotic Technologies; Science and Technology Literature Press; Catalogue of New Books of Science and Technology; Sep. 1987, pp. 360-363.

Hu et al. "Heat and mass transfer in gas metal arc welding. Part 1: the arc" found in ScienceDirect, International Journal of Heat and Mass transfer 50 (2007) 833-846 Available on Line on Oct. 24, 2006 http://web.mst.edu/~tsai/publications/Hu-IJHMT-2007-1-60.pdf.

Impact Welding: examples from current and archived website, trade shows, etc. See, e.g.,; http://www.impactweldinq.com. 53 pages; estimated Jan. 2000.

Irving, et al., "Efficient simulation of large bodies of water by coupling two and three dimensional techniques," ACM SIGGRAPH 2006 Papers, Jul. 30-Aug. 3, 2006, Boston, Massachusetts.

Jeffus, "Welding Principles and Applications" Sixth Edition, 2008, 10 pages.

Jonsson et al. "Simulation of Tack Welding Procedures in Butt Joint Welding of Plates" Research Supplement, Oct. 1985.

Juan Vicenete Rosell Gonzales, "RV-Sold: simulator virtual para la formacion de soldadores"; Deformacion Metalica, Es. vol. 34, No. 301 Jan. 1, 2008.

Kass, et al., "Rapid, Stable Fluid Dynamics for Computer Graphics," Proceedings of SIGGRAPH '90, in Computer Graphics, vol. 24, No. 4, pp. 49-57, 1990.

Klingner, et al., "Fluid animation with dynamic meshes," In Proceedings of ACM SIGGRAPH 2006, pp. 820-825, Aug. 2006.

Kobayashi, et al., "Simulator of Manual Metal Arc Welding with Haptic Display" ("Kobayashi 2001"), Proc. of the 11th International Conf. on Artificial Reality and Telexistence (ICAT), Dec. 5-7, 2001, pp. 175-178, Tokyo, Japan.

Kobayashi, et al., "Skill Training System of Manual Arc Welding by Means of Face-Shield-Like HMD and Virtual Electrode" ("Kobayashi 2003"), Entertainment Computing, vol. 112 of the International Federation for Information Processing (IFIP), Springer Science + Business Media, New York, copyright 2003, pp. 389-396.

Lincoln Global, Inc., "VRTEX 360: Virtual Reality Arc Welding Trainer" Brochure (2015) 4 pages.

Lindholm, et al., "NVIDIA Testla: A Unifired Graphics and Computing Architecture", IEEE Computer Society, 2008.

Mahrle, A., et al.; "the influence of fluid flow phenomena on the laser beam welding process" International Journal of Heat and Fluid Flow 23 (2002, No. 3, pp. 288-297; Institute of Fluid Dynamics and Thermodynamics, Otto-von-Guericke University Magdeburg, P.O. Box 4120, D-39016 Magdeburg, Germany.

Mann, et al., "Realtime HDR (High Dynamic Range) Video for Eyetap Wearable Computers, FPGA-Based Seeing Aids, and Glasseyes (EYETAPS)," 2012 25th IEEE Canadian Conference on Electrical and Computer Engineering (CCECE),pp. 1-6, Apr. 29, 2012, 6 pages.

Mantinband, et al., "Autosteroscopic, field-sequential display with full freedom of movement OR Let the display were the shutterglasses," 3ality (Israel) Ltd., 2002.

Mavrikios D et al, A prototype virtual reality-based demonstrator for immersive and interactive simulation of welding processes, International Journal of Computer Integrated manufacturing, Taylor and Francis, Basingstoke, GB, vol. 19, No. 3, Apr. 1, 2006, pp. 294-300.

Miller Electric Mfg. Co, "LiveArc: Welding Performance Management System" Owner's Manual, (Jul. 2014) 64 pages.

Miller Electric Mfg. Co., "LiveArc Welding Performance Management System" Brochure, (Dec. 2014) 4 pages.

Miller Electric Mfg. Co.; MIG Welding System features weld monitoring software; NewsRoom 2010 (Dialog® File 992); © 2011 Dialog. 2010; http://www.dialogweb.com/cgi/dwclient?reg=1331233430487; three (3) pages; printed Mar. 8, 2012.

Moore, "No exponential is forever: but 'Forever' can be delayed!," IEEE International Solid-State Circuits Conference, 2003.

Müller, et al., "Particle-based fluid simulation for interactive applications," Proceedings of the 2003 ACM SIGGRAPH/Eurographics symposium on Computer animation, Jul. 26-27, 2003, San Diego, California.

Müller, et al., "Point Based Animation of Elastic, Plastic and Melting Objects," Eurographics/ACM SIGGRAPH Symposium on Computer Animation (2004).

N. A. Tech., P/NA.3 Process Modeling and Optimization, 11 pages, Jun. 4, 2008.

Nasios, "Improving Chemical Plant Safety Training Using Virtual Reality," Thesis submitted to the University of Nottingham for the Degree of Doctor of Philosophy, Dec. 2001.

Nealen, A., "Point-Based Animation of Elastic, Plastic, and Melting Objects," CG topics, Feb. 2005.

Nordruch, et al., "Visual Online Monitoring of PGMAW Without a Lighting Unit", Jan. 2005.

NSRP ASE, Low-Cost Virtual Realtiy Welder Training System, 1 Page, 2008.

O'Brien et al.,"Dynamic Simulation of Splashing Fluids". In Proceedings of Computer Animation 95, pp. 198-205, Apr. 1995.

O'Brien, "Google's Project Glass gets some more details",Jun. 27, 2012 (Jun. 27, 2012), Retrieved from the Internet: http://www.engadget.com/2012/06/27/googles-project-glass-gets-some-more-details/, retrieved on Sep. 26, 2014, 1 page.

P/NA.3 Process Modelling and Optimization; Native American Technologies, allegedly 2002,; 5 pages.

Penrod, "New Welder Training Tools." EWI PowerPoint presentation; 16 pages allegedly 2008.

Phar, "GPU Gems 2 Programming Techniques for High-Performance Graphics and General-Purpose Computation," 2005, 12 pages.

Porter, et al. Virtual Reality Welder Trainer, Session 5: Joining Technologies for Naval Applications: earliest date Jul. 14, 2006 (http://weayback.archive.org) Edision Welding Institute; J. Allan Cote, General Dynamics Electric Boat; Timothy D. Gifford, VRSim, and Wim Lam, FCS Controls.

(56) References Cited

OTHER PUBLICATIONS

Porter, et al., Virtual Reality Training, Paper No. 2005-P19, 14 pages, 2005.
Porter, et al., Virtual Reality Training, vol. 22, No. 3, Aug. 2006; 13 pages.
Porter, et al., Virtual Reality Welder Training, dated Jul. 14, 2006.
Praxair Technology Inc., "The RealWeld Trainer System: Real Weld Training Under Real Conditions" Brochure (Est. Jan. 2013) 2 pages.
Premoze, et al., "Particle-based simulation of fluids," Comput. Graph. Forum 22, 3, 401-410, 2003.
Rasmussen, et al., "Directable photorealistic liquids," Proceedings of the 2004 ACM SIGGRAPH/Eurographics symposium on Computer animation, Aug. 27-29, 2004, Grenoble, France.
Ratnam, et al., "Automatic classification of weld defects using simulated data and an MLP neutral network." Insight vol. 49, No. 3; Mar. 2007.
Reeves, "Particles Systems—A Technique for Modeling a Class of Fuzzy Objects", Computer Graphics 17:3 pp. 359-376, 1983.
Renwick, et al., "Experimental Investigation of GTA Weld Pool Oscillations" Welding Research—Supplement to the Welding Journal, Feb. 1983, 7 pages.
Rodjito, "Position tracking and motion prediction using Fuzzy Logic," 2006, Colby College.
Russel, et al., "Artificial Intelligence: A Modern Approach", Prentice-Hall (Copywrite 1995).
Sandor, et al., "Lessons Learned in Designing Ubiquitous Augmented; Reality User Interfaces." 21 pages, allegedly from Emerging Technologies of Augmented; Reality: Interfaces Eds. Haller, M.; Billinghurst, M.; Thomas, B. Idea Group Inc. 2006.
Sandor, et al., "PAARTI: Development of an Intelligent Welding Gun for; BMW." PIA2003, 7 pages, Tokyo. 2003.
Sandter, et al. Fronius—virtual welding, FH JOANNEUM, Gesellschaft mbH, University of; Annlied Sciences 2 pages, May 12, 2008.
Schoder, "Design and Implementation of a Video Sensor for Closed Loop Control of Back Bead Weld Puddle Width," Massachusetts Institute of Technology, Dept. of Mechanical Engineering, May 27, 1983.
Screen Shot of CS Wave Control Centre V3.0.0 https://web.archive.org/web/20081128081915/http://wave.c-s.fr/images/english/snap_evolution4.jpg; Estimated Jan. 2007.
Screen Shot of CS Wave Control Centre V3.0.0 https://web.archive.org/web/20081128081817/http://wave.c-s.fr/images/english/snap_evolution6.jpg, estimated Jan. 2007.
Screen Shot of CS Wave Exercise 135.FWPG Root Pass Level 1 https://web.archive.org/web/20081128081858/http://wave.c-s.fr/images/english/snap_evolution2.jpg, estimated Jan. 2007.
Sim Welder, retrieved on Apr. 12, 2010 from: http://www.simwelder.com.
Simfor / Cesol, "RV-SOLD" Welding Simulator, Technical and Functional Features, 20 pages, estimated Jan. 2010.
Slater, et al., "Mechanisms and Mechanical Devices Sourcebook," McGraw Hill; 2nd Addition, 1996.
Stam, J., "Stable fluids," Proceedings of the 26th annual conference on Computer graphics and interactive techniques, p. 121-128, Jul. 1999.
Swantec corporate web page downloaded Apr. 19, 2016. http://www.swantec.com/technology/numerical-simulation/.
Tamasi, T., "The Evolution of Computer Graphics," NVIDIA, 2008.
Teeravarunyou, et al, "Computer Based Welding Training System," International Journal of Industrial Engineering (2009) 16(2): 116-125.
Terebes: examples from http://www.terebes.uni-bremen.de.; 6 pages.
The Fabricator, Virtual Welding, 4 pages, Mar. 2008.
The Lincoln Electric Company, "VRTEX Virtual Reality Arc Welding Trainer," http://www.lincolnelectric.com/en-us/equipment/training-equipment/Pages/vrtex.aspx as accessed on Jul. 10, 2015, 3 pages.
The Lincoln Electric Company, Production Monitoring 2 brochure, 4 pages, May 2009.
The Lincoln Electric Company; CheckPoint Production Monitoring borchure; four (4) pages; http://www.lincolnelectric.com/assets/en_US/products/literature/s232.pdf; Publication S2.32; Issue Date Feb. 2012.
Thurey, et al., "Real-time Breaking Waves for Shallow Water Simulations," In Proceedings of the 15th Pacific Conference on Computer Graphics and Applications (PG '07) 2007.
Tonnesen, D., "Modeling Liquids and Solids using Thermal Particles," Proceedings of Graphics Interface'91, pp. 255-262, Calgary, Alberta, 1991.
Tschirner, et al., "Virtual and Augmented Reality for Quality Improvement of Manual Welds" National Institute of Standards and Technology, Jan. 2002, Publication 973, 24 pages.
Tschirner, et al, "A Concept for the Application of Augmented Reality in Manual Gas Metal Arc Welding." Proceedings of the International Symposium on Mixed and Augmented Reality; 2 pages; 2002.
Vesterlund, M., "Simulation and Rendering of a Viscous Fluid using Smoothed Particle Hydrodynamics," Dec. 3, 2004, Master's Thesis in Computing Science, Umeå University, Department of Computing Science, Umeå, Sweden.
Viega, et al. "Simulation of a Work Cell in the IGRIP Program" dated 2006; 50 pages.
Virtual Welding: A Low Cost Virtual Reality Welder Training System, NSRP RA 07-01—BRP Oral Review Meeting in Charleston, SC at ATI, Mar. 2008.
ViziTech USA, "Changing the Way America Learns," http://vizitechusa.com/ accessed on Mar. 27, 2014; 2 pages.
VRSim Inc. "About Us—History" www.vrsim.net/history, 2016, 1 page.
VRSim Powering Virtual Reality, www.lincolnelectric.com/en-us/equipmenl/lraining-equipmenl/Pages/powered-by-; 'rsim.aspx, 2016, 1 page.
Wade, "Human uses of ultrasound: ancient and modern", Ultrasonics vol. 38, dated 2000.
Wahi, et al., "Finite-Difference Simulation of a Multi-Pass Pipe Weld" ("Wahi"), vol. L, paper 3/1, International Conference on Structural Mechanics in Reactor Technology, San Francisco, CA, Aug. 15-19, 1977.
Wang, et al. "Numerical Analysis of Metal Tranfser in Gas Metal Arc Welding, " Departements of Mechanical and Electrical Engineering. University of Kentucky, Dec. 10, 2001.
Wang, et al., "Impingement of Filler Droplets and Weld Pool During Gas Metal Arc Welding Process" International Journal of Heat and Mass Transfer, Sep. 1999, 14 pages.
Wang, et al., "Study on welder training by means of haptic guidance and virtual reality for arc welding," 2006 IEEE International Conference on Robotics and Biomimetics, ROBIO 2006 ISBN-10: 1424405718, p. 954-958.
Webster's II new college dictionary, 3rd ed., Houghton Mifflin Co., copyright 2005, Boston, MA, p. 1271, definition of "wake."
White, et al., Virtual welder training, 2009 IEEE Virtual Reality Conference, p. 303, 2009.
Wu, "Microcomputer-based welder training simulator", Computers in Industry, vol. 20, No. 3, Oct. 1992, pp. 321-325, XP000205597, Elsevier Science Publishers, Amsterdam, NL.
Wuhan Onew Technology Co Ltd, "ONEW-360 Welding Training Simulator" http://en.onewtech.com/_d276479751.htm as accessed on Jul. 10, 2015, 12 pages.
Yao, et al., "Development of a Robot System for Pipe Welding" 2010 International Conference on Measuring Technology and Mechatronics Automation. Retrieved from the Internet: http://ieeexplore.ieee.org/stamp/stamp.jsp?tp=&arnumber=5460347&tag=1; pp. 1109-1112.
Yoder, Fletcher, Opinion RE45398 and U.S. Appl. No. 14/589,317, including Appendices ; Sep. 9, 2015; 1700 pages.
United States Provisional Patent Application for "System for Characterizing Manual Welding Operations on Pipe and Other Curved Structures," U.S. Appl. No. 62/055,724, filed Sep. 26, 2014, 35 pages.
Office Action from U.S. Appl. No. 14/526,914 dated Feb. 3, 2017.
Arc Simulation & Certification, Weld Into the Future, 4 pages, 2005, Jan. 2008.

(56) References Cited

OTHER PUBLICATIONS

International Search Report and Written Opinion from PCT/IB10/02913 dated Apr. 19, 2011.
International Search Report for PCT/IB2014/001796, dated Mar. 24, 3016; 8 pages.
International Search Report for PCT/IB2015/000161, dated Aug. 25, 2016; 9 pages.
International Search Report for PCT/IB2015/000777, dated Dec. 15, 2016; 11 pages.
International Search Report for PCT/IB2015/000814 dated Dec. 15, 2016; 9 pages.
International Preliminary Report from PCT/IB2015/001084 dated Jan. 26, 2017.
Petition for Inter Partes Review of U.S. Pat. No. 8,747,116; IPR 2016-00749; Apr. 7, 2016; 70 pages.
Declaration of Edward Bohnart, Apr. 27, 2016, exhibit to IPR 2016-00749.
Declaration of Dr. Michael Zyda, May 3, 2016, exhibit to IPR 2016-00749.
Trial Denied IPR Proceeding of U.S. Pat. No. 8,747,116; IPR 2016-00749; Sep. 21, 2016; 21 pages.
Petition for Inter Partes Review of U.S. Pat. No. Re. 45,398; IPR 2016-00840; Apr. 18, 2016; 71 pages.
Declaration of AxelGraeser, Apr. 17, 2016, exhibit to IPR 2016-00840; 88 pages.
Decision Denying Request for Rehearing of U.S. Pat. No. Re. 45,398; IPR 2016-00840; Nov. 17,2016; 10 pages.
Petition for Inter Partes Review of U.S. Pat. No. 8,747,116; IPR 2016-01568; Aug. 9, 2016; 75 pages.
Decision Termination Proceeding of U.S. Pat. No. 8,747,116; IPR 2016-01568; Nov. 15, 2016; 4 pages.
Petition for Inter Partes Review of U.S. Pat. No. 9,293,056; IPR 2016-00904; May 9, 2016; 91 pages.
Declaration of Edward Bohnart, Apr. 27, 2016, exhibit to IPR 2016-00904; 22 pages.
Declaration of Dr. Michael Zyda, May 3, 2016, exhibit to IPR 2016-00904; 76 pages.
Decision Trial Denied IPR Proceeding of U.S. Pat. No. 9,293,056; IPR 2016-00904; Nov. 3, 2016; 15 pages.
Petition for Inter Partes Review of U.S. Pat. No. 9,293,057; IPR 2016-00905; May 9, 2016; 87 pages.
Declaration of Edward Bohnart, Apr. 27, 2016, exhibit to IPR 2016-00905; 23 pages.
Declaration of Dr. Michael Zyda, May 3, 2016, exhibit to IPR 2016-00905; 72 pages.
Decision Trial Denied IPR Proceeding of U.S. Pat. No. 9,293,057; IPR 2016-00905; Nov. 3, 2016; 21 pages.
*Lincoln Electric Company et al v. Seabery Soluciones SL et al*—1:15-cv-01575-DCN—Complaint filed Aug. 15, 2015 (Dkt 01).
*Lincoln Electric Company et al v. Seabery Soluciones SL et al*—1:15-cv-01575-DCN—Amended Answer filed Mar. 1, 2016 by Seabery North America (docket 44).
*Lincoln Electric Company et al v. Seabery Soluciones SL et al*—1:15-cv-01575-DCN—Amended Answer filed Mar. 1, 2016 by Seabery Soluciones SL (docket 45).
*Lincoln Electric Company et al v. Seabery Soluciones SL et al*—1:15-cv-01575-DCN—Amended Answer filed Mar. 22, 2016 by Lincoln Electri c Company (docket 46).
*Lincoln Electric Company et al v. Seabery Soluciones SL et al*—1:15-cv-01575-DCN—Answer filed Mar. 22, 2016 by Lincoln Global Inc. (docket 47).
Exhibit B from Declaration of Morgan Lincoln in *Lincoln Electric Co. et al. v. Seabery Soluciones, S.L. et al.*, Case No. 1:15-cv-01575-DCN, dated Dec. 20, 2016, 5 pages.
International Serach Report and Written Opinion for International Application No. PCT/IB2009/006605.
Extended European Search Report from Corresponding Application No. 18185849.9; dated Jan. 30, 2019; pp. 1-8.
European Examination Report from Corresponding Application No. 14728279.2; dated Mar. 13, 2019; pp. 1-4.
The Lincoln Electric Company, Check Point Operator's Manual, 188 pages, issue date Aug. 2015.
William Huff, Khoi Nguyen," Computer Vision Based Registration Techniques for Augmented Reality", Colorado School of Mines, Division of Engineering, Proceedings of Intellectual Robots and Computer Vision XV, pp. 538-548; SPIE vol. 2904, Nov. 18-22, 1996, Boston MA.
European Search Report for European Patent Application 10860823.3-1702, pp. 1-8, dated Jun. 6, 2017.
Benkai Xie, Qiang Zhou and Liang Yu; A Real Time Welding Training System Base on Virtual Reality; Onew 360; Wuhan University of Technology; IEEE Virtual Reality Conference; Mar. 23-27, 2015.
Lindh; "Strength in numbers: How the Industrial Internet of Things applies to fabricators"; thefabricatior.com; http://www.thefabricator.com/article/shopmanagement/theres-strength-in-numbers-how-the-industrial-internet-of-things-applies-to-fabricators; Dated Feb. 11, 2016; pp. 1-2.
"ITAMCO Engineer Wins Prize for Google Glass Application"; http://www.fabricatingandmetalworking.com/2014/05/itamco-engineer-wins-75000-for-google-glass-application/; Dated May 6, 2014; pp. 1-2.
Bennett; "OK, Glass, take a video of me welding this pipeline"; https://www.biv.com/article/2013/8/ok-glass-take-a-video-of-me-welding-this-pipeline/; Dated Aug. 12, 2013; pp. 1-2.
Mann; "Steve Mann: My "Augmediated" Life"; https://spectrum.ieee.org/geek-life/profiles/steve-mann-my-augmediated-life; Dated Mar. 1, 2013; pp. 1-6.
Wheeler; "Understanding Augmented Reality Headsets"; https://www.engineering.com/DesignSoftware/DesignSoftwareArticles/ArticleID/12859/Understanding-Augmented-Reality-Headsets.aspx; Dated Aug. 10, 2016; pp. 1-7.
Kemppi; "Welding production management: WeldEye Welding Management Software"; https://www.kemppi.com/en-US/offering/product/welding-production-management/; Accessed Apr. 11, 2017; pp. 1-16.
"ESAB Welding & Cutting GmbH: Helping ESAB Realize an IoT Connected Vision"; PAC Innovation Register; https://www.pac-online.com/sites/pac-online.com/files/upload_path/PDFspac_innovation_register_case_study_esab_iot_connected_vision_16_0.pdf; Dated 2016; pp. 1-4.
"ThingWorx Delivers Industrial Innovation"; https://www.ptc.com/en/products/iot; Accessed Apr. 11, 2017; pp. 1-5.
Zhu; "Computer and Network Oriented Welding Power Source Design"; Applied Mechanics and Materials; vols. 58-60; Dated 2011; pp. 864-868.

* cited by examiner

SYSTEMS AND METHODS PROVIDING A COMPUTERIZED EYEWEAR DEVICE TO AID IN WELDING

CROSS-REFERENCE TO RELATED APPLICATIONS AND INCORPORATION BY REFERENCE

This application is a continuation-in-part (CIP) of U.S. application Ser. No. 15/245,535, filed on Aug. 24, 2016, entitled "SYSTEMS AND METHODS PROVIDING A COMPUTERIZED EYEWEAR DEVICE TO AID IN WELDING," which is a continuation of U.S. application Ser. No. 14/105,758, filed Dec. 13, 2013, which claims priority to and the benefit of U.S. provisional patent application Ser. No. 61/827,248 filed on May 24, 2013. The entireties of the aforementioned applications are incorporated herein by reference. U.S. Pat. No. 9,285,592, entitled "WEARABLE DEVICE WITH INPUT AND OUTPUT STRUCTURES," filed on Aug. 18, 2011, and which issued on Mar. 15, 2016, is incorporated by reference herein in its entirety. U.S. Pat. No. 8,747,116, entitled "SYSTEM AND METHOD PROVIDING ARC WELDING TRAINING IN A REAL-TIME SIMULATED VIRTUAL REALITY ENVIRONMENT USING REAL-TIME WELD PUDDLE FEEDBACK," filed on Jul. 10, 2009, and which issued on Jun. 10, 2014, is incorporated by reference herein in its entirety.

TECHNICAL FIELD

Certain embodiments of the present invention relate to welding. More particularly, certain embodiments of the present invention relate to systems and methods providing visualization and communication capabilities to a welder using a welding system via a computerized eyewear device.

BACKGROUND

Providing information to a welding student in real time during a welding process (whether a real-world welding process or a simulated welding process) is important to aid the welding student in the learning process. Similarly, providing information to an expert welder in real time during a real-world welding process can aid the expert welder in the welding process. Furthermore, providing the ability for a welding student or an expert welder to easily communicate with (e.g., provide commands to) a welding system (real or simulated) can allow for a more efficient and user-friendly welding experience. Today, a welding helmet may be provided with simple light indicators representative of welding information which don't require a welder to be able to focus sharply on the light indicators, since the light indicators may be within one inch of the welder's eye. Simply being able to see that the color of a light indicator is red or green or yellow, for example, is provided. Thus, there is an ongoing need to improve how a welder or welding student interacts with a welding system and how information is provided and viewed in real time.

Further limitations and disadvantages of conventional, traditional, and proposed approaches will become apparent to one of skill in the art, through comparison of such systems and methods with embodiments of the present invention as set forth in the remainder of the present application with reference to the drawings.

SUMMARY

In one embodiment, a system is provided. The system includes an internet-of-things (IoT) technology platform including at least one server computer having a connection server application. The IoT technology platform is configured to be implemented as part of a real world welding environment. The IoT technology platform is also configured to provide scalable, interoperable, and secure wireless communication connections between a plurality of disparate devices within the real world welding environment. The IoT technology platform is further configured to enable protocol-independent deployment of the plurality of disparate devices within the real world welding environment. The system also includes at least one welding power source, being at least one of the plurality of disparate devices, configured to wirelessly communicate, two-way, with the IoT technology platform using the connection server application. The system further includes at least one computerized eyewear device, being at least one of the plurality of disparate devices. The computerized eyewear device includes a control and communication circuitry having a processor and a memory. The control and communication circuitry is configured to wirelessly communicate, two-way, with the welding power source via the IoT technology platform using the connection server application. The computerized eyewear device also includes a transparent display configured to display information received by the control and communication circuitry from the welding power source via the IoT technology platform using the connection server application. A user is able to view a surrounding portion of the real world welding environment through the transparent display. In one embodiment, the IoT technology platform is configured to provide the scalable, interoperable, and secure communication connections between the plurality of disparate devices via WebSockets. The IoT technology platform is configured to handle message routing and translation between the plurality of disparate devices. The IoT technology platform is configured to allow a developer to build, run, and grow applications to control and report data to and from any of the plurality of disparate devices. The information displayed by the transparent display may be in the form of at least one of text, a graphic, or an image and may include at least one welding parameter received from the welding power source via the IoT technology platform. In one embodiment, the computerized eyewear device includes a microphone operatively connected to the control and communication circuitry. The microphone, as operatively connected to the control and communication circuitry, is configured to receive voice-activated user command information from the user and communicate the voice-activated user command information to the welding power source via the IoT technology platform. In one embodiment, the computerized eyewear device includes a camera operatively connected to the control and communication circuitry. The camera, as operatively connected to the control and communication circuitry, is configured to capture at least one still image (picture) or moving video of the real world welding environment during a welding operation from the point-of-view of the user and communicate the still image (picture) or moving video to the IoT technology platform for recording and storage. In one embodiment, the computerized eyewear device includes a touch-sensitive user interface operatively connected to the control and communication circuitry. The touch-sensitive user interface, as operatively connected to the control and communication circuitry, is configured to allow a user to select command information and provide the command information to the welding power source via the IoT technology platform to control the welding power source. The welding power source may be an inverter-based welding power source that supports at least one of a gas metal arc welding (GMAW) operation, a gas tungsten arc welding (GTAW) operation, or a shielded metal arc welding (SMAW) operation.

In another embodiment, a system is provided. The system includes a plurality of disparate devices within a real world welding environment having disparate wireless communication capabilities. The system also includes an IoT technology platform including at least one server computer having a connection server application. The IoT technology platform is configured to provide scalable, interoperable, and secure wireless communication connections between the plurality of disparate devices. The IoT technology platform is also configured to enable protocol-independent deployment of the plurality of disparate devices within the real world welding environment. The plurality of disparate devices includes at least one welding power source configured to wirelessly communicate, two-way, with the IoT technology platform using the connection server application. The plurality of disparate devices further includes at least one computerized eyewear device. The computerized eyewear device includes a control and communication circuitry having a processor and a memory. The control and communication circuitry is configured to wirelessly communicate, two-way, with the welding power source via the IoT technology platform using the connection server application. The computerized eyewear device also includes a transparent display configured to display information received by the control and communication circuitry from the welding power source via the IoT technology platform using the connection server application. A user is able to view a surrounding portion of the real world welding environment through the transparent display. In one embodiment, the computerized eyewear device is configured to provide an augmented reality capability via at least the transparent display. The plurality of disparate devices may include, for example, at least one of at least one welding wire feeder, at least one welding torch or gun, at least one gas meter/sensor operatively connected to at least one tank of shielding gas, at least one mobile phone device (e.g., a "smart" phone), at least one welding helmet, or at least one welding fume extractor. In one embodiment, at least one of the plurality of disparate devices includes at least one sensor configured to sense at least one parameter associated with the at least one of the plurality of disparate devices and communicate the at least one parameter to the IoT technology platform using the connection server application. The at least one parameter may include, for example, at least one of a temperature parameter, a pressure parameter, a humidity parameter, a voltage parameter, a current parameter, a wire feed speed parameter, a flow rate parameter, a spatial position parameter, a spatial orientation parameter, or a travel speed parameter.

In one embodiment, a system is provided. The system includes a welding power source of an arc welding system and a computerized eyewear device having a head-up display (HUD). The computerized eyewear device is configured to be worn by a user as eye glasses are worn, while the user also wears a protective welding helmet. The computerized eyewear device is further configured to wirelessly communicate with the welding power source of the arc welding system. The computerized eyewear device may receive information from the welding power source and display the information on the HUD. Furthermore, the user may provide commands to the welding power source via the computerized eyewear device (e.g., via voice activation). The welding power source and the computerized eyewear device may be cooperatively configured to provide one or more of augmented indicators indicative of a user's welding technique and sequencer functionality indicative of a next weld to be made on the HUD, for example.

In another embodiment, a system is provided. The system includes a programmable processor-based subsystem of a virtual reality welding simulation system and a computerized eyewear device having a head-up display (HUD). The computerized eyewear device is configured to be worn by a user as eye glasses are worn, while the user also wears a protective welding helmet. The computerized eyewear device is further configured to wirelessly communicate with the programmable processor-based subsystem of the virtual reality welding simulation system. The computerized eyewear device may receive information from the programmable processor-based subsystem and display the information on the HUD. Furthermore, the user may provide commands to the programmable processor-based subsystem via the computerized eyewear device (e.g., via voice activation). The programmable processor-based subsystem and the computerized eyewear device may be cooperatively configured to provide one or more of virtual reality images associated with a virtual reality welding process and virtual cues and indicators associated with a virtual reality welding process on the HUD, for example.

In accordance with an embodiment, the computerized eyewear device includes a frame configured to be worn on the head of a user, the frame including a bridge configured to be supported on the nose of the user, a brow portion coupled to and extending away from the bridge to a first end remote therefrom and configured to be positioned over a first side of a brow of the user, and a first arm having a first end coupled to the first end of the brow portion and extending to a free end, the first arm being configured to be positioned over a first temple of the user with the free end disposed near a first ear of the user, wherein the bridge is adjustable for selective positioning of the brow portion relative to an eye of the user. The computerized eyewear device also includes a transparent display (the HUD) which may be affixed to the frame and may be movable with respect to the frame through rotation about a first axis that extends parallel to the first brow portion. The computerized eyewear device also includes a housing containing control and communication circuitry affixed to the frame. As an example, the computerized eyewear device may be a Google Glass™ device configured for operation with an arc welding system or a virtual reality arc welding simulation system.

Details of illustrated embodiments of the present invention will be more fully understood from the following description and drawings.

DETAILED DESCRIPTION

Figure 1:
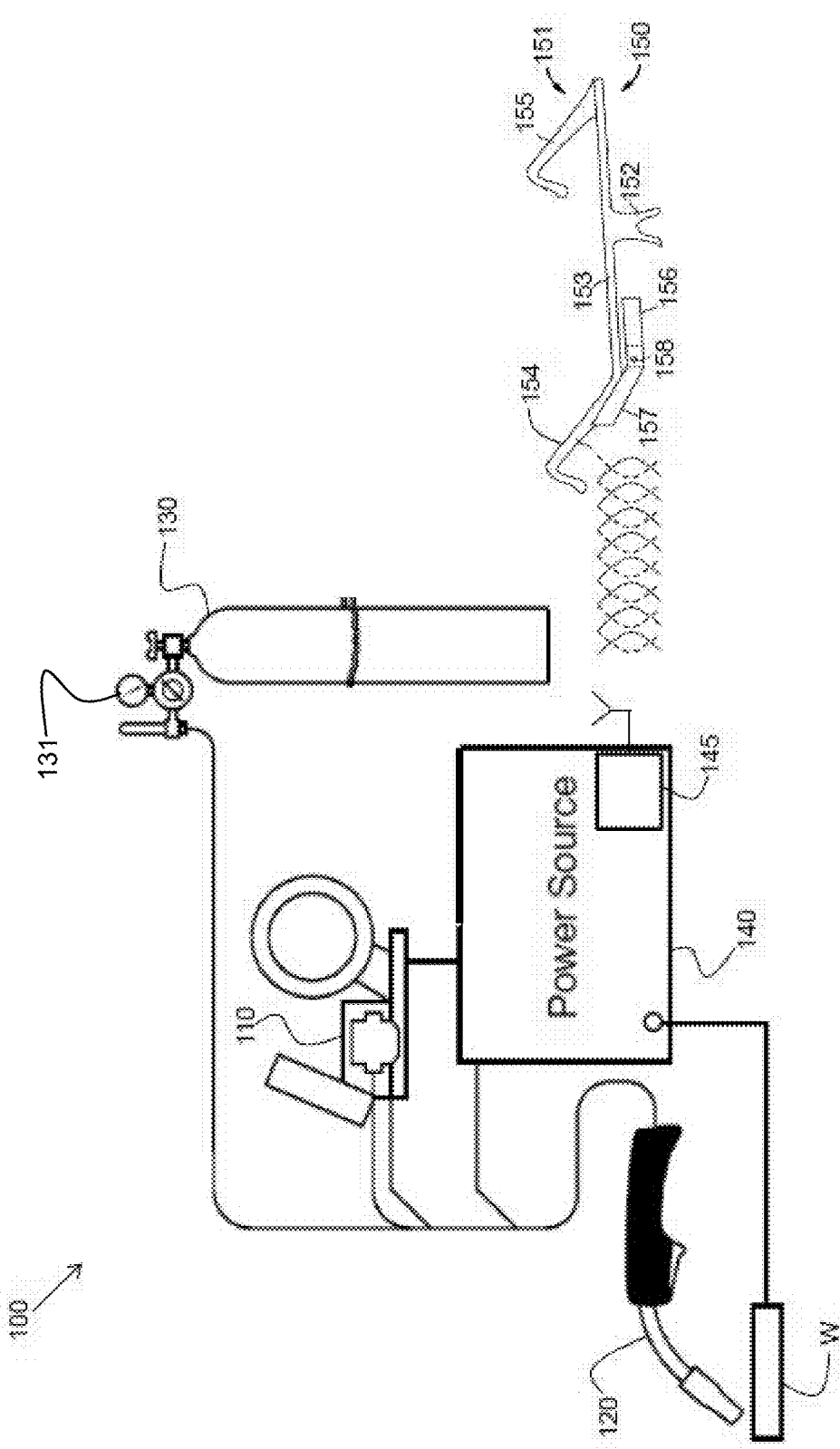
FIG. 1 illustrates a diagram of an exemplary embodiment of an arc welding system and a computerized eyewear device configured to communicate with the arc welding system.

The following are definitions of exemplary terms that may be used within the disclosure. Both singular and plural forms of all terms fall within each meaning:

"Software" or "computer program" as used herein includes, but is not limited to, one or more computer readable and/or executable instructions that cause a computer or other electronic device to perform functions, actions, and/or behave in a desired manner. The instructions may be embodied in various forms such as routines, algorithms, modules or programs including separate applications or code from dynamically linked libraries. Software may also be implemented in various forms such as a stand-alone program, a function call, a servlet, an applet, an application, instructions stored in a memory, part of an operating system or other type of executable instructions. It will be appreciated by one of ordinary skill in the art that the form of software is dependent on, for example, requirements of a desired application, the environment it runs on, and/or the desires of a designer/programmer or the like.

"Computer" or "processing element" or "computerized device" as used herein includes, but is not limited to, any programmed or programmable electronic device that can store, retrieve, and process data. "Non-transitory computer-readable media" include, but are not limited to, a CD-ROM, a removable flash memory card, a hard disk drive, a magnetic tape, and a floppy disk.

"Computer memory", as used herein, refers to a storage device configured to store digital data or information which can be retrieved by a computer or processing element.

"Controller", as used herein, refers to the logic circuitry and/or processing elements and associated software or program involved in controlling a device, system, or portion of a system.

The terms "signal", "data", and "information" may be used interchangeably herein and may be in digital or analog form.

The term "welding parameter" is used broadly herein and may refer to characteristics of a portion of a welding output current waveform (e.g., amplitude, pulse width or duration, slope, electrode polarity), a welding process (e.g., a short arc welding process or a pulse welding process), wire feed speed, a modulation frequency, a welding travel speed, or some other parameter associated with real-world welding or simulated welding.

The term "head up display", as used herein, refers to a transparent display that presents information (e.g., high quality images) without requiring a user to look away from their usual viewpoints.

In one embodiment, an arc welding system is provided. The arc welding system includes a welding power source and a computerized eyewear device having a head-up display (HUD) and control and communication circuitry (CCC) operatively connected to the HUD. The computerized eyewear device is configured to be worn by a user as eye glasses are worn, while also wearing a protective welding helmet, and wirelessly communicate with the welding power source. The control and communication circuitry is configured to wirelessly receive information from the welding power source and display the information on the HUD.

In accordance with an embodiment, the computerized eyewear device includes a microphone operatively connected to the control and communication circuitry. The microphone and the control and communication circuitry are configured to receive voice-activated user command information and wirelessly transmit the voice-activated user command information to the welding power source. In accordance with an embodiment, the computerized eyewear device includes a camera operatively connected to the control and communication circuitry. The camera and the control and communication circuitry are configured to capture one or more of still pictures and moving video. In accordance with an embodiment, the control and communication circuitry is configured to access the internet through a wireless access point.

In accordance with an embodiment, the computerized eyewear device includes a frame configured to be worn on the head of a user and at least one housing affixed to the frame containing one or more of the control and communication circuitry, the microphone, and the camera. The HUD is also affixed to the frame and is movable with respect to the frame through rotation about a first axis that extends parallel to a first brow portion. Optionally, the computerized eyewear device may include at least one prescription optical lens held in place by the frame.

In accordance with an embodiment, the frame includes a bridge configured to be supported on the nose of the user, a brow portion coupled to and extending away from the bridge to a first end remote therefrom and configured to be positioned over a first side of a brow of the user, and a first arm having a first end coupled to the first end of the brow portion and extending to a free end. The first arm is configured to be positioned over a first temple of the user with the free end disposed near a first ear of the user. In accordance with an embodiment, the bridge is adjustable for selective positioning of the brow portion relative to an eye of the user.

FIG. 1 illustrates a diagram of an exemplary embodiment of an arc welding system 100 and a computerized eyewear device 150 configured to communicate with the arc welding system 100. The arc welding system 100 includes a wire feeder 110, a welding gun or tool 120, a shielding gas supply 130 (e.g., a tank of shielding gas) with a gas meter/sensor 131, and a welding power source 140. The wire feeder 110, the welding gun 120, the shielding gas supply 130, and the power source 140 are operatively connected to allow a welder to create an electric arc between a welding wire and a workpiece W to create a weld as is well known in the art.

In accordance with an embodiment, the welding power source 140 includes a switching power supply (not shown), a waveform generator (not shown), a controller (not shown), a voltage feedback circuit (not shown), a current feedback circuit (not shown), and a wireless communication circuit 145. The wire feeder 110 feeds the consumable wire welding electrode E toward the workpiece W through the welding gun (welding tool) 120 at a selected wire feed speed (WFS). The wire feeder 110, the consumable welding electrode E, and the workpiece W are not part of the welding power source 140 but may be operatively connected to the welding power source 140 via a welding output cable.

The computerized eyewear device 150 is configured to be worn by a user as eye glasses are worn, while also wearing a conventional protective welding helmet. The protective welding helmet may be a conventional welding helmet that does not have to be modified in any way to accommodate the computerized eyewear device 150. Furthermore, the computerized eyewear device 150 is configured to wirelessly communicate with the welding power source 140 via the wireless communication circuit 145 of the welding power source 140. The wireless communication circuit 145 may include a processor, computer memory, a transmitter, a receiver, and an antenna, in accordance with an embodiment.

Figure 2:
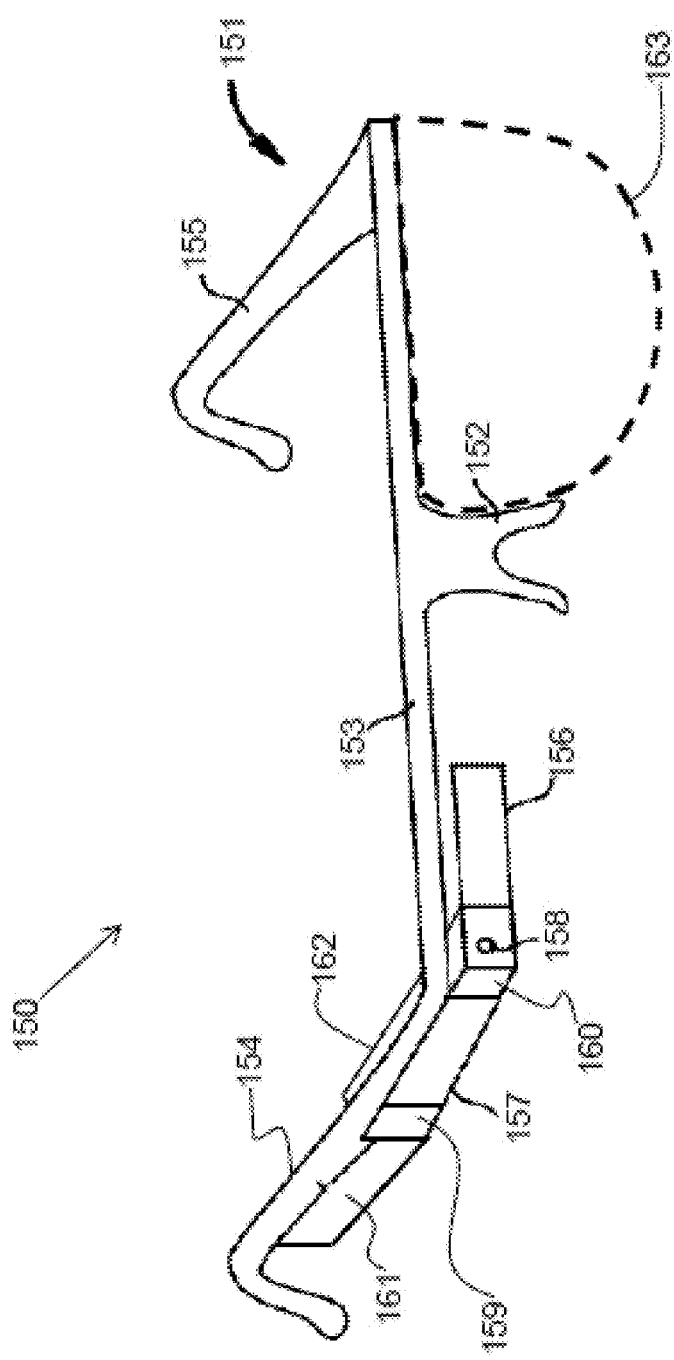
FIG. 2 illustrates a diagram of an exemplary embodiment of the computerized eyewear device of FIG. 1.

Referring now to FIG. 1 and FIG. 2, where FIG. 2 illustrates a diagram of an exemplary embodiment of the computerized eyewear device 150 of FIG. 1, the computerized eyewear device 150 includes a frame 151 configured to be worn on the head of a user. The frame 151 includes a bridge 152 configured to be supported on the nose of the user and a brow portion 153 coupled to and extending away from the bridge 152 to a first and second ends remote therefrom and configured to be positioned over the brows of the user.

The frame also includes a first arm 154 having a first end coupled to the first end of the brow portion 153 and extending to a free end, the first arm being configured to be positioned over a first temple of the user with the free end disposed near a first ear of the user. The frame 151 also includes a second arm 155 having a first end coupled to the second end of the brow portion 153 and extending to a free end, the second arm being configured to be positioned over a second temple of the user with the free end disposed near a second ear of the user. The bridge 152 may be adjustable for selective positioning of the brow portion 153 relative to the eyes of the user, in accordance with an embodiment.

The computerized eyewear device 150 includes a transparent display (e.g., a HUD) 156 affixed to the frame 151. The HUD 156 may be movable with respect to the frame 151 through rotation about a first axis that extends parallel to the brow portion 153, in accordance with an embodiment, and may be configured to display text, graphics, and images. The computerized eyewear device 150 also includes control and communication circuitry (e.g., a computer) 157 enclosed in a housing 162 and affixed to the frame 151. The control and communication circuitry 157 may include a processor and memory, for example. The memory may be coupled to the processor and store software that can be accessed and executed by the processor. The processor may be a microprocessor or a digital signal processor, for example. As an option, the computerized eyewear device 150 may include a camera 158. The HUD 156 and the control and communication circuitry 157 (and, optionally, the camera 158) are operatively connected to provide the functionality described herein. In accordance with an embodiment, the camera 158 is configured to capture still pictures (images) and moving video. In this way, a user may record the welding scenario as viewed by the user from inside the welding helmet.

In accordance with an embodiment, the control and communication circuitry 157 provides two-way communication with the wireless communication circuit 145 of the welding power source 140. Information may be provided from the welding power source 140 to the computerized eyewear device 150 and displayed on the HUD 156. Furthermore, in accordance with an embodiment, the control and communication circuitry 157 is configured to accept voice-activated commands from a user and transmit the commands to the welding power source 140. Communication between the welding power source 140 and the computerized eyewear device 150 may be accomplished by way of, for example, Bluetooth® radio technology, communication protocols described in IEEE 802.11 (including any IEEE 802.11 revisions), cellular technology (such as GSM, CDMA, UMTS, EVDO, WiMax, or LTE), or ZigBee® technology, among other possibilities. In accordance with an embodiment, the computerized eyewear device may also include at least one optical lens 163 that matches a user's corrective visual prescription. In accordance with a further embodiment, the computerized eyewear device may be modular and attachable to normal prescription eye glasses.

Furthermore, in accordance with an embodiment, the welding power source 140 may be accessible by the computerized eyewear device 150 via the Internet. For example, the control and communication circuitry 157 may be configured to access the Internet through a wireless hot spot (e.g., a smart phone or a wireless router) and access the welding power source 140 therethrough. Alternatively, the welding power source 140 may be configured to access the Internet and provide information obtained from the Internet to the computerized eyewear device 150.

Information that may be displayed on the HUD 156 during a real-world welding scenario that may be useful to a welder may be in the form of text, an image, or a graphic. Such information may include, for example, the arc welding process, a welding tool travel angle, a welding tool travel speed, a tip-to-work distance, a wire feed speed, a welding polarity, an output voltage level, an output current level, an arc length, a dime spacing, a whip time, a puddle time, a width of weave, a weave spacing, a tolerance window, a number score, and welding sequence steps. Other information may be displayed as well, in accordance with other embodiments. For example, in an augmented mode, instructional indicators that are used in a virtual reality training environment may be superimposed over an actual weld using the HUD 156. In this manner, a welding student who trained on a virtual reality welding system can transition to a real welding scenario and have the same instructional indicators provided via the HUD. Visual cues or indicators may be displayed to the welder on the HUD of the computerized eyewear device to indicate to the welder if a particular parameter (e.g., a welding tool travel angle) is within an acceptable range or not. Such visual cues or indicators may aid in training by helping an inexperienced welder or welding student to improve his welding technique.

The acquisition of some of the information may rely on the welding tool being spatially tracked (e.g., travel angle, travel speed, tip-to-work distance). In accordance with an embodiment, the welding tool may include an accelerometer device that is operatively connected to the welding power source to provide spatial position or movement information. Other methods of tracking the welding tool are possible as well, such as magnetic tracking techniques, for example.

In accordance with an embodiment, the computerized eyewear device 150 includes a microphone 159 for receiving voice-activated commands from a user. The voice-activated commands, as initiated by a welder, that may be accommodated by the computerized eyewear device 150 in communication with the welding power source 140 may include, for example, commands to change a welding parameter such as a wire feed speed, a welding polarity, and a welding output current level. Other types of commands may be possible as well, in accordance with other embodiments.

In accordance with an embodiment, the computerized eyewear device 150 and/or the welding power source 140 may be programmed with one or more welding software applications configured to accommodate use of the computerized eyewear device 150 with the arc welding system 100. For example, an embodiment of one welding software application may provide a "good weld" recognition capability. Similar to a facial recognition capability, the "good weld" recognition capability may use the camera 158 to acquire an image of a weld created by the user, analyze the image, and provide feedback to the user on the HUD 156 as to the overall external quality of the weld. For example, the text "poor weld", "fair weld", or "good weld" may be displayed to the user. The user may have to take off his welding helmet or lift a visor on the welding helmet to acquire an image of the weld. The welding software application may reside in the computerized eyewear device 150, the welding power source 140, or a combination of both, in accordance with various embodiments.

As another example, an embodiment of a welding software application may provide a welding sequencing capability. When welding a part or assembly with many welds, it is not desirable for a welder to miss a weld. A welding software application may step a welder through the multiple welds for the part. For example, as a welder finishes a current weld on a part or assembly requiring multiple welds, the welder may give a voice command of "next weld". As a result, the welding software application may display to the welder on the HUD 156 an image or graphic (e.g., a 3D representation of the part) providing the location of the next weld to be performed. The type of weld and other information associated with the weld may also be displayed. In accordance with an embodiment where the computerized eyewear device 150 is being spatially tracked, as discussed later herein, the welding software application may display a graphic on the HUD such that graphic indicator is overlaid onto the assembly at the next location to be welded. Other types of welding software applications that operate with the computerized eyewear device are possible as well, in accordance with other embodiments.

In one embodiment, a virtual reality welding system is provided. The virtual reality welding system includes a programmable processor-based subsystem and a computerized eyewear device having a head-up display (HUD) and control and communication circuitry (CCC) operatively connected to the HUD. The computerized eyewear device is configured to be worn by a user as eye glasses are worn, and to wirelessly communicate with the programmable processor-based subsystem. The control and communication circuitry is configured to wirelessly receive information from the programmable processor-based subsystem and display the information on the HUD.

In accordance with an embodiment, the computerized eyewear device further includes a microphone operatively connected to the control and communication circuitry and configured to receive voice-activated user command information and wirelessly transmit the voice-activated user command information to the programmable processor-based subsystem. Alternatively, or in addition, the computerized eyewear device may include a touch-sensitive user interface operatively connected to the control and communication circuitry and configured to allow a user to select command information and wirelessly transmit the command information to the programmable processor-based subsystem.

In accordance with an embodiment, the computerized eyewear device includes a camera operatively connected to the control and communication circuitry. The camera and the control and communication circuitry are configured to capture one or more of still pictures and moving video. In accordance with an embodiment, the control and communication circuitry is configured to access the internet through a wireless access point.

In accordance with an embodiment, the computerized eyewear device includes a frame configured to be worn on the head of a user and at least one housing affixed to the frame containing one or more of the control and communication circuitry, the microphone, and the camera. The HUD is also affixed to the frame and is movable with respect to the frame through rotation about a first axis that extends parallel to a first brow portion. Optionally, the computerized eyewear device may include at least one prescription optical lens held in place by the frame.

In accordance with an embodiment, the frame includes a bridge configured to be supported on the nose of the user, a brow portion coupled to and extending away from the bridge to a first end remote therefrom and configured to be positioned over a first side of a brow of the user, and a first arm having a first end coupled to the first end of the brow portion and extending to a free end. The first arm is configured to be positioned over a first temple of the user with the free end disposed near a first ear of the user. In accordance with an embodiment, the bridge is adjustable for selective positioning of the brow portion relative to an eye of the user.

In accordance with an embodiment, the computerized eyewear device includes at least one motion sensing device operatively connected to the control and communication circuitry and configured to provide spatial information to the programmable processor-based subsystem as a user moves his head.

Figure 3:
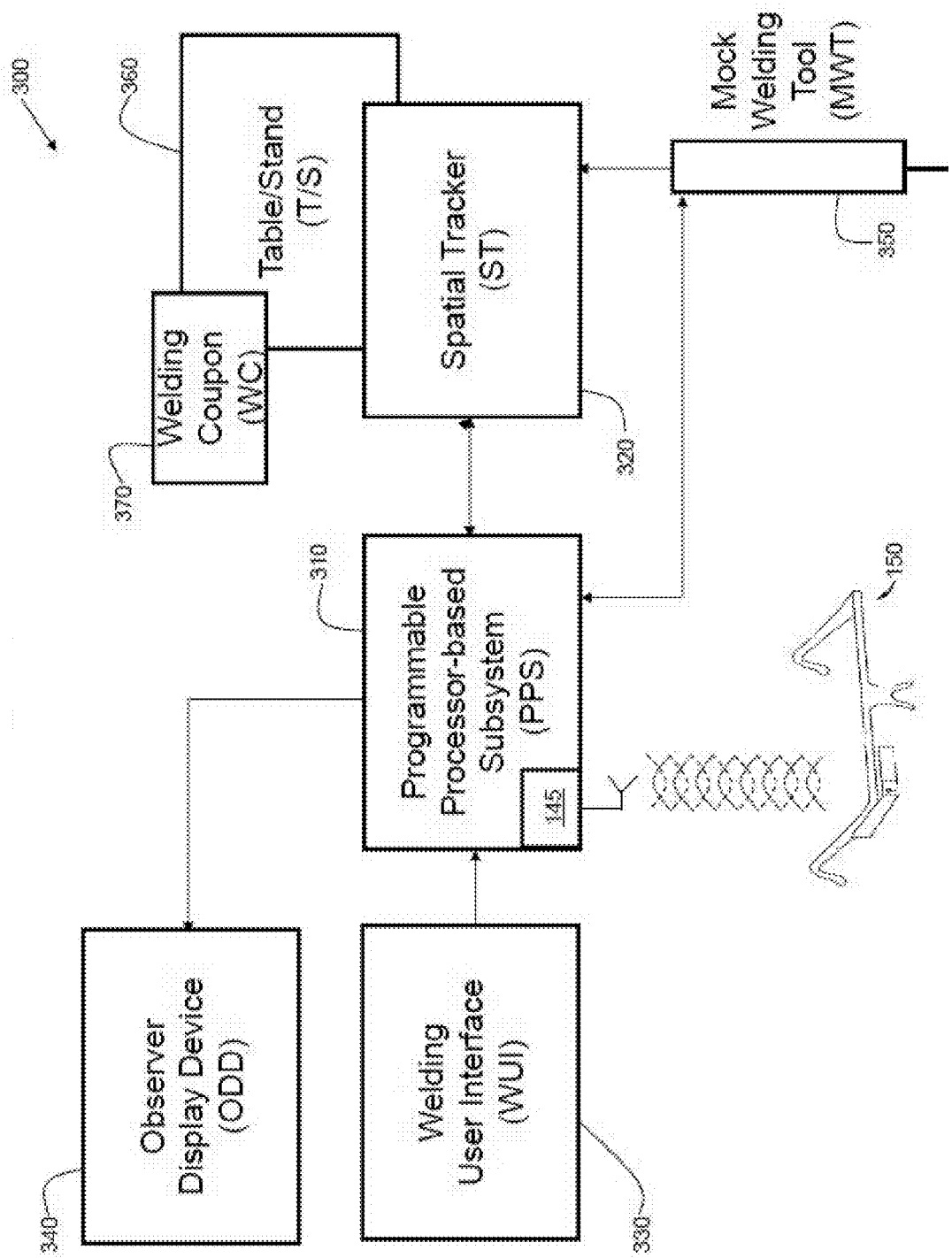
FIG. 3 illustrates a diagram of an exemplary embodiment of a virtual reality welding system and a computerized eyewear device configured to communicate with the virtual reality welding system.

FIG. 3 illustrates a diagram of an exemplary embodiment of a virtual reality arc welding system 300 and a computerized eyewear device 150 configured to communicate with the virtual reality welding system 300. The virtual reality arc welding (VRAW) system includes a programmable processor-based subsystem, a spatial tracker operatively connected to the programmable processor-based subsystem, at least one mock welding tool capable of being spatially tracked by the spatial tracker, and at least one display device operatively connected to the programmable processor-based subsystem. In accordance with an embodiment, the computerized eyewear device 150 may also be spatially tracked by the spatial tracker. The system is capable of simulating, in a virtual reality space, a weld puddle having real-time molten metal fluidity and heat dissipation characteristics. The system is also capable of displaying the simulated weld puddle on the display device in real-time.

The system 300 includes a programmable processor-based subsystem (PPS) 310. The system 300 further includes a spatial tracker (ST) 320 operatively connected to the PPS 310. The system 300 also includes a physical welding user interface (WUI) 330 operatively connected to the PPS 310 as well as the computerized eyewear device 150 in operative wireless communication with the PPS 310 via a wireless communication circuit 145 of the PPS 310. The system 300 further includes an observer display device (ODD) 340 operatively connected to the PPS 310. The system 300 also includes at least one mock welding tool (MWT) 350 operatively connected to the ST 320 and the PPS 310. The system 300 further includes a table/stand (T/S) 360 and at least one welding coupon (WC) 370 capable of being attached to the T/S 360. In accordance with an alternative embodiment of the present invention, a mock gas bottle is provided (not shown) simulating a source of shielding gas and having an adjustable flow regulator.

In accordance with an embodiment, the computerized eyewear device 150 is configured as previously described herein. However, in this embodiment, the control and communication circuitry 157 provides two-way communication with the wireless communication circuit 145 of the PPS 310. Information may be provided from the PPS 310 to the computerized eyewear device 150 and displayed on the HUD 156.

Furthermore, in accordance with an embodiment, the control and communication circuitry 157 is configured to accept voice-activated commands from a user and transmit the commands to the PPS 310. Communication between the PPS 310 and the computerized eyewear device 150 may be accomplished by way of, for example, Bluetooth® radio technology, communication protocols described in IEEE 802.11 (including any IEEE 802.11 revisions), cellular technology (such as GSM, CDMA, UMTS, EVDO, WiMax, or LTE), or ZigBee® technology, among other possibilities.

Furthermore, in accordance with an embodiment, the PPS 310 may be accessible by the computerized eyewear device 150 via the Internet. For example, the control and communication circuitry 157 may be configured to access the Internet through a wireless hot spot (e.g., a smart phone or a wireless router) and access the PPS 310 therethrough. Alternatively, the PPS 310 may be configured to access the Internet and provide information obtained from the Internet to the computerized eyewear device 150.

As before, the user may wear a conventional welding helmet over the computerized eyewear device 150. However, since the welding scenario is a simulated welding scenario, the conventional welding helmet may be fitted with a transparent lens instead of a protective lens that protects against the light and other radiation emitted by a real arc. As such, the user may see through the transparent lens to view the welding coupon 370 and the mock welding tool 350, for example.

In accordance with an embodiment, the computerized eyewear device 150 is configured with an accelerometer device 160 that is operatively connected to the control and communication circuitry 157. Spatial information provided by the accelerometer device as the user moves his head is communicated to the PPS 310 and then to the spatial tracker 320. In this manner, the spatial relationship between the surrounding environment and what the user is seeing through the HUD 156 of the computerized eyewear device 150 may be correlated. As the user proceeds with the virtual welding process using the system 300, anything displayed on the HUD 156 (e.g., a virtual weld puddle) will appear overlaid onto, for example, the welding coupon 370 as the user views the welding coupon through the transparent lens of the conventional welding helmet. In accordance with other embodiments, other motion sensing devices besides that of an accelerometer device may be used. A calibration procedure may be initially performed to correlate the view of the user through the HUD to the surrounding environment, in accordance with an embodiment.

The real-time molten metal fluidity and heat dissipation characteristics of the simulated weld puddle provide real-time visual feedback to a user of the mock welding tool when displayed (e.g., on the HUD of the computerized eyewear device 150 as tracked by the spatial tracker 320), allowing the user to adjust or maintain a welding technique in real-time in response to the real-time visual feedback (i.e., helps the user learn to weld correctly). When the computerized eyewear device 150 is being spatially tracked, the weld puddle will appear at a correct location with respect to the welding coupon as viewed through the HUD.

The displayed weld puddle is representative of a weld puddle that would be formed in the real-world based on the user's welding technique and the selected welding process and parameters. By viewing a puddle (e.g., shape, color, slag, size, stacked dimes), a user can modify his technique to make a good weld and determine the type of welding being done. The shape of the puddle is responsive to the movement of the gun or stick.

The term "real-time", as used herein with respect to a virtual reality or simulated environment, means perceiving and experiencing in time in a virtual or simulated environment in the same way that a user would perceive and experience in a real-world welding scenario. Furthermore, the weld puddle is responsive to the effects of the physical environment including gravity, allowing a user to realistically practice welding in various positions including overhead welding and various pipe welding angles (e.g., 1G, 2G, 5G, 6G).

Information that may be useful to a welding student to display on the HUD 156 during a virtual or simulated welding scenario may be in the form of text, an image, or a graphic. Such information may include, for example, the arc welding process, a welding tool travel angle, a welding tool travel speed, a tip-to-work distance, a set wire feed speed, a set welding polarity, a simulated output voltage level, a set output current level, a simulated arc length, a dime spacing, a whip time, a puddle time, a width of weave, a weave spacing, a tolerance window, a number score, and welding sequence steps. Other information may be displayed as well, in accordance with other embodiments.

In accordance with an embodiment, the computerized eyewear device 150 includes a microphone 159 that is operatively connected to the control and communication circuitry 157 for receiving voice-activated commands from a user. The voice-activated commands, as initiated by a welder, that may be accommodated by the computerized eyewear device 150 in communication with the PPS 310 may include, for example, commands to change a welding parameter such as a simulated wire feed speed, a simulated welding polarity, and a simulated welding output current level. Other types of commands may be possible as well, in accordance with other embodiments.

In accordance with an embodiment, the computerized eyewear device 150 and/or the PPS 310 may be programmed with one or more welding training software applications configured to accommodate use of the computerized eyewear device 150 with the virtual reality arc welding system 300. For example, an embodiment of one welding software application may provide a "good weld" recognition capability. Similar to a facial recognition capability, the "good weld" recognition capability may use an image of a simulated weld created by the user, analyze the image, and provide feedback to the user on the HUD 156 as to the overall external quality of the weld. For example, the text "poor weld", "fair weld", or "good weld" may be displayed to the user. The welding software application may reside in the computerized eyewear device 150, the PPS 310, or a combination of both, in accordance with various embodiments.

As another example, an embodiment of a welding software application may provide a welding sequencing capability. As a welder finishes a current simulated weld on a welding coupon requiring multiple welds, the welder may give a voice command of "next weld". As a result, the welding software application may display to the welder on the HUD 156 an image or graphic providing the location of the next weld to be performed. The type of weld and other information associated with the weld may also be displayed. In accordance with an embodiment where the computerized eyewear device 150 is being spatially tracked, as discussed herein, the welding software application may display a graphic on the HUD such that the graphic is overlaid onto the welding coupon at the next location to be welded. Other types of welding software applications that operate with the computerized eyewear device are possible as well, in accordance with other embodiments.

The computerized eyewear device 150 may be configured to be used with other welding simulation systems in accordance with other embodiments. For example, welding simulations performed on a personal computer (PC) or a tablet computer may be communicatively and functionally integrated with the computerized eyewear device 150 to aid a welding student in learning how to weld. In some simulated and/or virtual welding environments, a welding student may not wear a welding helmet of any kind. Instead, the computerized eyewear device may be the only head gear worn. One optional embodiment of the computerized eyewear device may provide a touch-sensitive user interface (TSUI) 161 which the welding student can use instead of or in addition to voice-activated commands. Such a TSUI would be accessible to the welding student when not wearing a welding helmet, for example. In accordance with an embodiment, the TSUI 161 is operatively connected to the control and communication circuitry 157.

Figure 4:
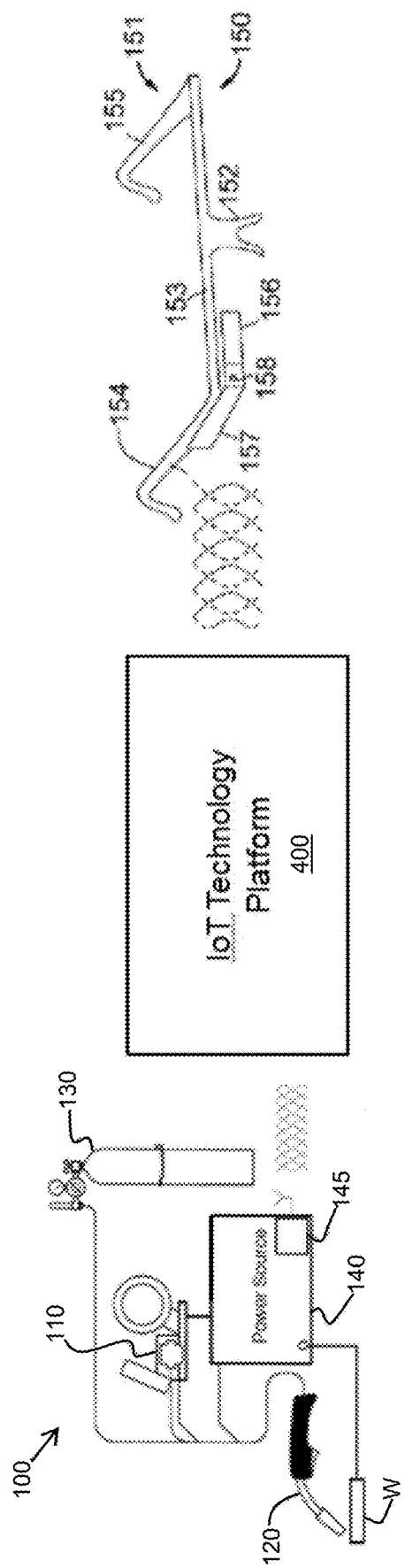
FIG. 4 illustrates a diagram of an exemplary embodiment of an arc welding system and a computerized eyewear device configured to communicate with each other via an internet-of-things (IoT) technology platform.

FIG. 4 illustrates a diagram of an exemplary embodiment of the arc welding system 100 of FIG. 1 and the computerized eyewear device 150 of FIG. 1 or FIG. 2, for example, configured to communicate with each other via an internet-of-things (IoT) technology platform 400. The arc welding system 100, having a welding power source 140, and the computerized eyewear device 150 may exist in a real world welding environment (e.g., a manufacturing facility). The term "real world" is used herein to refer to an actual welding environment as opposed to a virtual welding environment. The IoT technology platform 400 may also exist in the real world welding environment along with the welding power source 140, the computerized eyewear device 150, and possibly other devices (e.g., other welding power sources, other computerized eyewear devices, etc.). In an alternative embodiment, a portion of the IoT technology platform 400 exists within the welding environment and another portion of the IoT technology platform 400 exists externally to the welding environment (e.g. as part of a server farm remotely located from the welding environment). That is, the IoT technology platform 400 may be distributed across several real world environments.

The IoT technology platform 400 provides scalable, interoperable, and secure wired and/or wireless communication connections (e.g., via WebSockets) between multiple disparate devices within the real world welding environment. The IoT technology platform 400 enables protocol-independent deployment of the multiple disparate devices within the real world welding environment. That is, devices that may communicate using different communication protocols can be accommodated by the IoT technology platform 400, allowing the disparate devices to communicate with each other through the IoT technology platform 400. The IoT technology platform 400 is configured to handle message routing and translation between the multiple disparate devices and allow a developer to build, run, and grow applications to control and report data to and from any of the multiple disparate devices. An example of an IoT technology platform is provided by ThingWorx®.

As shown in FIG. 4, the welding power source 140 of the arc welding system 100, being one of the multiple disparate devices, is configured to wirelessly communicate (two-way) with the IoT technology platform 400. In one embodiment, the welding power source 140 is an inverter-based welding power source that supports at least one of a gas metal arc welding (GMAW) operation, a gas tungsten arc welding (GTAW) operation, or a shielded metal arc welding (SMAW) operation. The computerized eyewear device 150, being one of the multiple disparate devices, includes a control and communication circuitry 157 and a transparent display 156.

In one embodiment, the control and communication circuitry 157 is configured to wirelessly communicate (two-way) with the welding power source 140 via the IoT technology platform 400. The transparent display 156 is configured to display information received by the control and communication circuitry 157 from the welding power source 140 via the IoT technology platform 400 while allowing a user to view a surrounding portion of the real world welding environment through the transparent display. That is, the computerized eyewear device 150 is configured to provide an augmented reality capability via at least the transparent display. For example, the information displayed by the transparent display 156 may be in the form of any of text, graphics, or images and may include welding parameters received from the welding power source 140 via the IoT technology platform 400.

In one embodiment, the computerized eyewear device 150 includes a microphone 159 (see FIG. 2) operatively connected to the control and communication circuitry 157. Together, the microphone 159 and the control and communication circuitry 157 are configured to receive voice-activated user command information from the user and communicate the voice-activated user command information to the welding power source 140 via the internet-of-things (IoT) technology platform 400.

In one embodiment, the computerized eyewear device 150 includes a camera 158 operatively connected to the control and communication circuitry 157. Together, the camera 158 and the control and communication circuitry 157 are configured to capture at least one still image or moving video of the real world welding environment during a welding operation from the point-of-view of the user and communicate the at least one still image or video to the internet-of-things (IoT) technology platform 400 for recording and storage.

In one embodiment, the computerized eyewear device 150 includes a touch-sensitive user interface 161 (see FIG. 2) operatively connected to the control and communication circuitry 157. Together, the touch-sensitive user interface 161 and the control and communication circuitry 157 are configured to allow a user to select command information and provide the command information to the welding power source 140 via the internet-of-things (IoT) technology platform 400 to control the welding power source 140.

Figure 5:
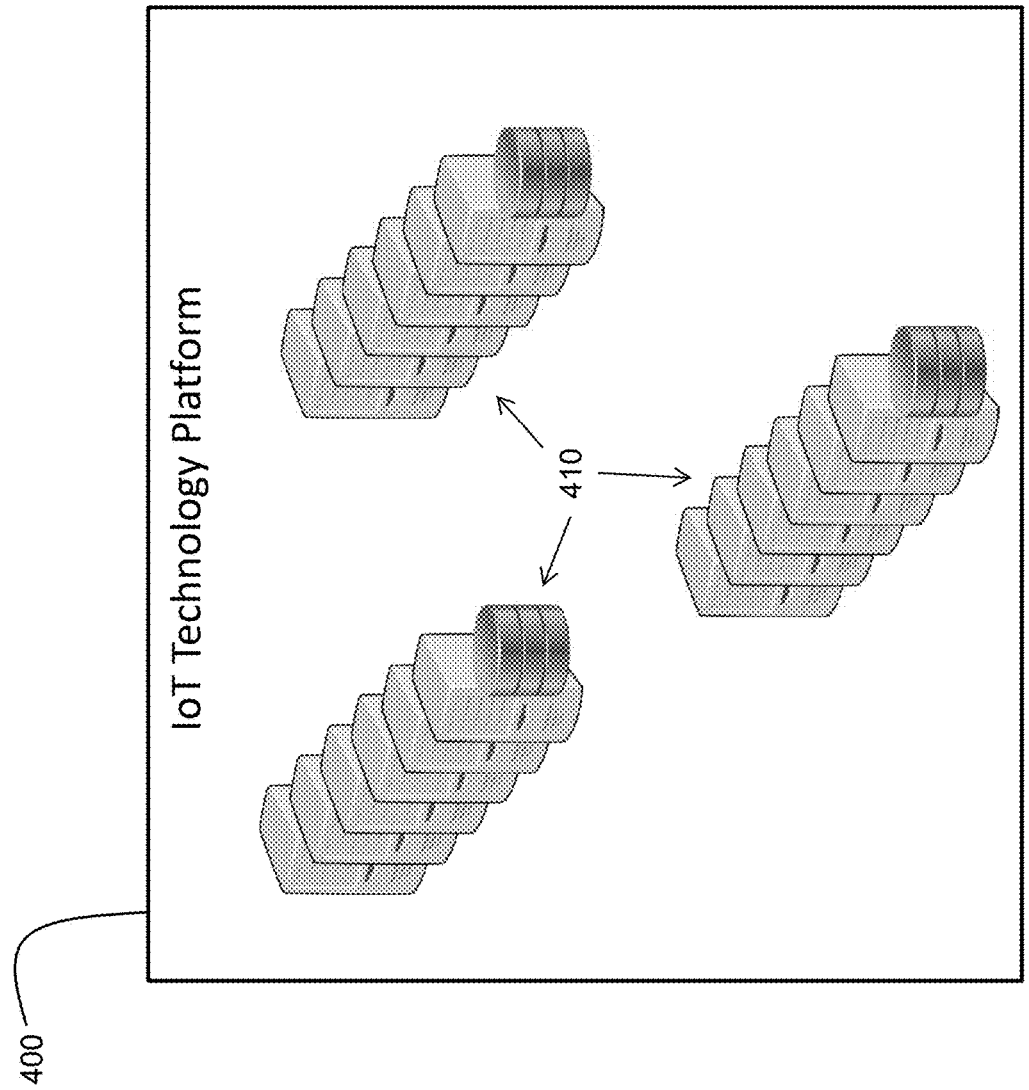
FIG. 5 illustrates a diagram of an exemplary embodiment of an internet-of-things (IoT) technology platform having multiple server computers.
Figure 6:
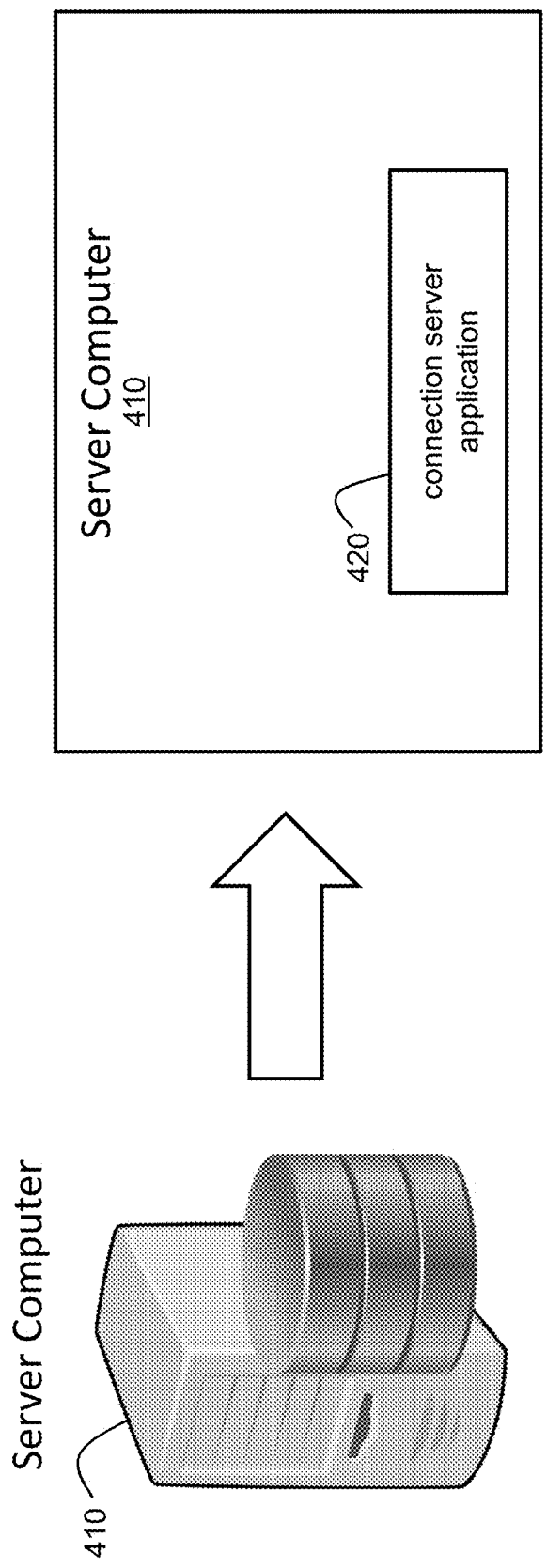
FIG. 6 illustrates a diagram of an exemplary embodiment of a server computer, of the internet-of-things (IoT) technology platform of FIG. 5, having a connection server application.

FIG. 5 illustrates a diagram of an exemplary embodiment of the internet-of-things (IoT) technology platform 400 of FIG. 4 having multiple server computers 410. The multiple server computers 410 support communication and interaction between the multiple disparate devices within the welding environment. FIG. 6 illustrates a diagram of an exemplary embodiment of one server computer 410 (of the multiple server computers), of the internet-of-things (IoT) technology platform 400 of FIG. 5, having a connection server application 420. In one embodiment, the connection server application 420 is configured to support the scalable, interoperable, and secure communication connections between the multiple disparate devices, enabling protocol-independent deployment of the multiple disparate devices within the real world welding environment. The connection server application 420 may include, for example, software or a combination of software and hardware, in accordance with various embodiments.

Figure 7:
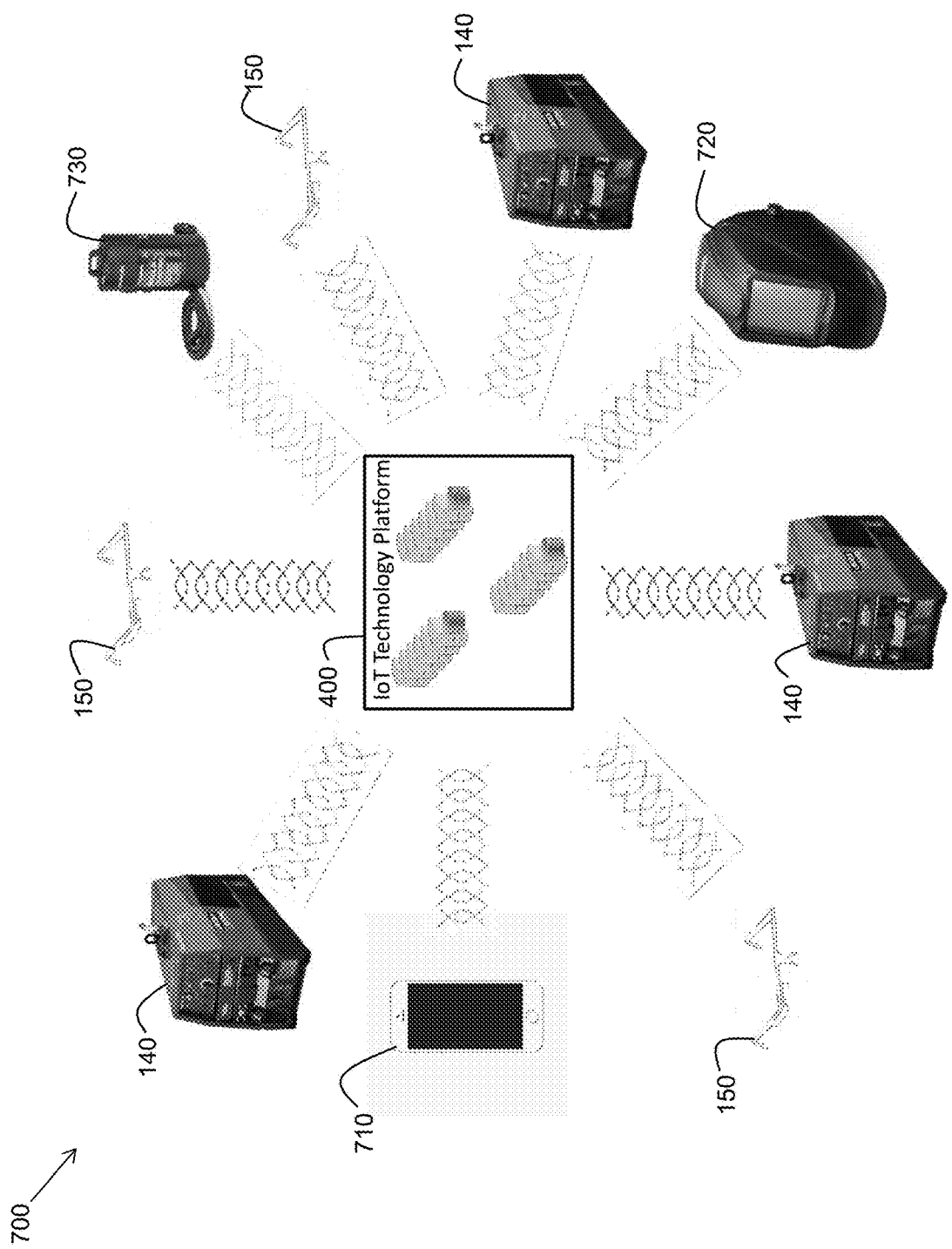
FIG. 7 illustrates a diagram of an exemplary embodiment of a welding environment having multiple welding power sources and multiple computerized eyewear devices that are configured to communicate with each other via an internet-of-things (IoT) technology platform.

FIG. 7 illustrates a diagram of an exemplary embodiment of a real world welding environment 700 having multiple disparate devices (e.g., multiple welding power sources 140 and multiple computerized eyewear devices 150) that are configured to communicate with each other via an internet-of-things (IoT) technology platform 400. As illustrated in FIG. 7, communication between the IoT technology platform 400 and any of the multiple disparate devices is via wireless means. In alternative embodiments, wired means and/or a combination of wired and wireless means may be employed. The IoT technology platform 400 facilitates communication between the multiple disparate devices. For example, in one embodiment, any disparate device may communicate with any other disparate device within the welding environment 700 via the IoT technology platform.

The multiple disparate devices in the real world welding environment 700 have disparate wireless communication capabilities. Wireless communication supported by the disparate devices and the IoT technology platform 400 may be via any of, for example, Bluetooth® radio technology, communication protocols described in IEEE 802.11 (including any IEEE 802.11 revisions), cellular technology (such as GSM, CDMA, UMTS, EVDO, WiMax, or LTE), or Zig-Bee® technology, among other possibilities. Again, the IoT technology platform 400 is configured to enable protocol-independent deployment of the multiple disparate devices within the real world welding environment at least by handling message routing and translation between the multiple disparate devices.

The disparate devices in the real world welding environment 700 may also include one or more welding wire feeders 110 (see FIG. 1), one or more welding guns or torches 120 (see FIG. 1), one or more gas meters/sensors 131 operatively connected to one or more tanks of shielding gas 130 (see FIG. 1), one or more mobile phone devices 710 ("smart" phones), one or more welding helmets 720 ("smart" welding helmets), and one or more welding fume extractors 730 ("smart" fume extractors). The term "smart" is used herein to refer to devices that have data communication capability and at least some limited capability to process and/or analyze the data which is communicated. Other types of disparate devices, in the real world welding environment 700, are possible as well, in accordance with other embodiments.

Any of the multiple disparate devices in the real world welding environment 700 may include one or more sensors (e.g., gas meter/sensor 131) to sense one or more corresponding parameters associated with the multiple disparate devices. The parameters may be communicated to the IoT technology platform 400 (e.g., using the connection server application 420). The parameters may include, for example, a temperature parameter, a pressure parameter, a humidity parameter, a voltage parameter, a current parameter, a wire feed speed parameter, a flow rate parameter, a spatial position parameter, a spatial orientation parameter, or a travel speed parameter. Other types of sensors and corresponding parameters are possible as well, in accordance with other embodiments.

In summary, systems and methods to aid a welder or welding student are provided. A system may include a real-world arc welding system or a virtual reality arc welding system along with a computerized eyewear device having a head-up display (HUD). The computerized eyewear device may be worn by a user under a conventional welding helmet as eye glasses are worn and may wirelessly communicate with a welding power source of a real-world arc welding system or a programmable processor-based subsystem of a virtual reality arc welding system.

A system to support communication and control in a welding environment is also disclosed. In one embodiment the system includes an internet-of-things (IoT) technology platform configured to provide scalable, interoperable, and secure communication connections between a plurality of disparate devices within a welding environment. The system also includes a welding power source configured to communicate with the IoT technology platform. The system further includes a computerized eyewear device. The computerized eyewear device includes a control and communication circuitry configured to communicate with the welding power source via the IoT technology platform. The computerized eyewear device also includes a transparent display configured to display information received from the welding power source via the IoT technology platform while allowing a user to view a surrounding portion of the welding environment through the transparent display.

In appended claims, the terms "including" and "having" are used as the plain language equivalents of the term "comprising"; the term "in which" is equivalent to "wherein." Moreover, in appended claims, the terms "first," "second," "third," "upper," "lower," "bottom," "top," etc. are used merely as labels, and are not intended to impose numerical or positional requirements on their objects. Further, the limitations of the appended claims are not written in means-plus-function format and are not intended to be interpreted based on 35 U.S.C. § 112, sixth paragraph, unless and until such claim limitations expressly use the phrase "means for" followed by a statement of function void of further structure. As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. Moreover, certain embodiments may be shown as having like or similar elements, however, this is merely for illustration purposes, and such embodiments need not necessarily have the same elements unless specified in the claims.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances the modified term may sometimes not be appropriate, capable, or suitable. For example, in some circumstances an event or capacity can be expected, while in other circumstances the event or capacity cannot occur—this distinction is captured by the terms "may" and "may be."

This written description uses examples to disclose the invention, including the best mode, and also to enable one of ordinary skill in the art to practice the invention, including making and using any devices or systems and performing any incorporated methods. The scope of the invention is defined by the claims, and may include other examples that occur to one of ordinary skill in the art. Such other examples are intended to be within the scope of the claims if they have structural elements that do not differentiate from the literal language of the claims, or if they include equivalent structural elements with insubstantial differences from the literal language of the claims.

While the invention of the present application has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiments disclosed, but that the invention will include all embodiments falling within the scope of the appended claims.

What is claimed is:

1. A welding system, comprising:
    an internet-of-things (IoT) technology platform including at least one server computer having a connection server application, wherein the internet-of-things (IoT) technology platform, includes means for providing scalable, interoperable, and secure wireless communication connections between a plurality of disparate devices, and includes means for enabling protocol-independent deployment of the plurality of disparate devices;
    at least one welding power source, being at least one of the plurality of disparate devices, including means for wirelessly communicating, two-way, with the internet-of-things (IoT) technology platform using the connection server application, wherein the at least one welding power source is an inverter-based welding power source that includes means for supporting at least one of a gas metal arc welding (GMAW) operation, a pas tungsten arc welding (GTAW) operation, or a shielded metal arc welding (SMAW) operation; and
    at least one computerized eyewear device, being at least one of the plurality of disparate devices, including:
        a control and communication circuitry, having a processor and a memory, configured to wirelessly communicate, two-way, with the at least one welding power source via the internet-of-things (IoT) technology platform using the connection server application, and
        a transparent display configured to display information received by the control and communication circuitry from the at least one welding power source via the internet-of-things (IoT) technology platform using the connection server application while allowing a user to view a surrounding portion of a real world welding environment through the transparent display.

2. The welding system of claim 1, wherein the means for providing scalable, interoperable, and secure communication connections between the plurality of disparate devices includes WebSockets.

3. The system of claim 1, wherein the internet-of-things (IoT) technology platform includes means for handling message routing and translation between the plurality of disparate devices.

4. The system of claim 1, wherein the internet-of-things (IoT) technology platform includes means for allowing a developer to build, run, and grow applications to control and report data to and from any of the plurality of disparate devices.

5. The system of claim 1, wherein the information displayed by the transparent display is in the form of at least one of text, a graphic, an image, or a video.

6. The system of claim 1, wherein the information displayed by the transparent display includes at least one welding parameter received from the at least one welding power source via the internet-of-things (IoT) technology platform.

7. The system of claim 1, wherein the at least one computerized eyewear device includes a microphone operatively connected to the control and communication circuitry and configured to receive voice-activated user command information from the user and communicate the voice-activated user command information to the at least one welding power source via the internet-of-things (IoT) technology platform.

8. The system of claim 1, wherein the at least one computerized eyewear device includes a camera operatively connected to the control and communication circuitry and configured to capture at least one still image or moving video of the real world welding environment during a welding operation from the point-of-view of the user and communicate the at least one still image or video to the internet-of-things (IoT) technology platform for recording and storage.

9. The system of claim 1, wherein the at least one computerized eyewear device includes a touch-sensitive user interface operatively connected to the control and communication circuitry and configured to allow a user to select command information and provide the command information to the at least one welding power source via the internet-of-things (IoT) technology platform to control the at least one welding power source.

10. A welding system, comprising:
    a plurality of disparate devices within a real world welding environment having disparate wireless communication capabilities; and
    an internet-of-things (IoT) technology platform including at least one server computer having a connection server application, wherein the internet-of-things (IoT) technology platform includes means for providing scalable, interoperable, and secure wireless communication connections between the plurality of disparate devices, and includes means for enabling protocol-independent deployment of the plurality of disparate devices within the real world welding environment,
    wherein the plurality of disparate devices includes at least one welding power source including means for wirelessly communicating, two-way, with the internet-of-things (IoT) technology platform using the connection server application, and
    wherein the plurality of disparate devices includes at least one computerized eyewear device including:
        a control and communication circuitry, having a processor and a memory, configured to wirelessly communicate, two-way, with the at least one welding power source via the internet-of-things (IoT) technology platform using the connection server application, and
        a transparent display configured to display information received by the control and communication circuitry from the at least one welding power source via the internet-of-things (IoT) technology platform using the connection server application while allowing a user to view a surrounding portion of the real world welding environment through the transparent display.

11. The system of claim 10, wherein the at least one computerized eyewear device includes means for providing an augmented reality capability via at least the transparent display.

12. The system of claim 10, wherein the plurality of disparate devices includes at least one welding wire feeder.

13. The system of claim 10, wherein the plurality of disparate devices includes at least one welding gun or torch.

14. The system of claim 10, wherein the plurality of disparate devices includes at least one gas meter operatively connected to at least one tank of shielding gas.

15. The system of claim 10, wherein the plurality of disparate devices includes at least one mobile phone device.

16. The system of claim 10, wherein the plurality of disparate devices includes at least one welding helmet.

17. The system of claim 10, wherein the plurality of disparate devices includes at least one welding fume extractor.

18. The system of claim 10, wherein at least one of the plurality of disparate devices includes at least one sensor configured to sense at least one parameter associated with the at least one of the plurality of disparate devices and communicate the at least one parameter to the internet-of-things (IoT) technology platform using the connection server application.

19. The system of claim 18, wherein the at least one parameter includes at least one of a temperature parameter, a pressure parameter, a humidity parameter, a voltage parameter, a current parameter, a wire feed speed parameter, a flow rate parameter, a spatial position parameter, a spatial orientation parameter, or a travel speed parameter.

* * * * *